United States Patent [19]

Humes et al.

[11] Patent Number: 5,549,674
[45] Date of Patent: Aug. 27, 1996

[54] METHODS AND COMPOSITIONS OF A BIOARTIFICIAL KIDNEY SUITABLE FOR USE IN VIVO OR EX VIVO

[75] Inventors: H. David Humes; Deborah A. Cieslinski, both of Ann Arbor, Mich.

[73] Assignee: The Regents of The University of Michigan, Ann Arbor, Mich.

[21] Appl. No.: 133,436

[22] Filed: Oct. 8, 1993

Related U.S. Application Data

[63] Continuation-in-part of Ser. No. 844,758, Mar. 2, 1992, Pat. No. 5,429,938.

[51] Int. Cl.$^6$ .............................. A61F 2/00; C12N 5/00; A61K 38/00; A61M 1/00
[52] U.S. Cl. ................... 623/11; 435/240.2; 435/240.21; 514/12; 600/36; 604/6; 604/35; 604/48; 604/319; 623/1; 623/12
[58] Field of Search ............................ 435/240.2, 240.21; 514/12; 600/36; 604/6, 35, 48, 319; 623/1, 11, 12

[56] References Cited

U.S. PATENT DOCUMENTS 5,035,708  7/1991  Alchas et al. ................ 623/1
5,192,747  3/1993  Krstenansky ................ 514/15

FOREIGN PATENT DOCUMENTS 0058275  8/1982  European Pat. Off. .

OTHER PUBLICATIONS

JP, A, 61, 115569 (Terumo Corp) Jun. 3, 1986 (Abstract).
Artificial Organs, 13(1): 58–65, 1989 (IP) "Renal Epithelial–Cell Controlled Solute Transport Across Permeable Membranes as the Foundation for a Bioartificial Kidney".
Database WPI, Derwent Publications, AN–86–180755/28, JP–61–115569, Jun. 3, 1986.
Deborah A. Cieslinski and H. David Humes, "Tissue Engineering Of A Bioartificial Kidney", Biotechnology and Bioengineering, vol. 43, pp. 678–681, (1994).

*Primary Examiner*—Shelley A. Dodson
*Attorney, Agent, or Firm*—Oblon, Spivak, McClelland, Maier, & Neustadt, P.C.

[57] ABSTRACT

A novel cell seeded hollow fiber bioreactor is described as a potential bioartificial kidney. Renal cells are seeded along a hollow fiber in a perfused bioreactor to reproduce the ultrafiltration function and transport function of the kidney. Maintenance of tissue specific function and ultrastructure suggest that this bioreactor provides an economical device for treating renal failure as well as studying renal tubululogenesis in vitro.

59 Claims, 15 Drawing Sheets

METHODS AND COMPOSITIONS OF A BIOARTIFICIAL KIDNEY SUITABLE FOR USE IN VIVO OR EX VIVO

This application is a continuation-in-part of U.S. Ser. No. 07/844,758, filed Mar. 2, 1992 now U.S. Pat. No. 5,429,938, incorporated herein by reference.

BACKGROUND OF THE INVENTION

1. Field of the Invention

This invention relates to devices formed from a combination of biological and mechanical elements—"bioartificial" devices. In particular, the present invention relates to a bioartificial kidney which comprises a bioartificial filtration device and a bioartificial tubule processing device.

2. Background of the Invention

End stage renal disorder (ESRD) is a common clinical syndrome involving a decline in renal function, either acutely or chronically. The clinical manifestations of this disorder arise from a decrease in the glomerular filtration rate and an inability of the kidney to excrete the toxic metabolic wastes produced by the body. The complete treatment of ESRD is dependent upon the replacement of the filtrative, reabsorptive, homeostatic and endocrine functions of the kidney as an integrated organ structure.

The excretory function of the kidney, the formation of urine, begins in the kidney with filtration of blood at the glomerulus which is a tuft of capillaries. These capillaries invaginate a surrounding capsule called Bowman's capsule where the renal tubule system begins. The structure of the glomerulus is designed to provide efficient ultrafiltration of blood to remove toxic wastes from the circulation and retain important components within the systemic circulation, such as albumin (Brenner and Humes, *New Engl. J. Med.* 297:148–154, 1977; Brenner et al., *New Engl. J. Med.* 298:826–833, 1978, both incorporated herein by reference).

The regulatory function of the kidney, especially with regard to fluid and electrolyte homeostasis, is provided by the tubular segments attached to the glomerulus. It is in the renal tubules where processes of osmosis, diffusion as well as active transport all assist in converting glomerular filtrate into urine. The ultrafiltrate emanating from the glomerulus courses along the kidney tubule which reabsorbs fluid and solutes to finely regulate the excretion of various amounts of solutes and water in the final urine. The functional unit of the kidney is, therefore, composed of the filtering unit, the glomerulus, and the regulatory unit, the tubule. Together they form the basic component of the kidney, called the nephron.

To date, the only successful long-term ex vivo replacement therapy for support of renal function is hemodialysis and chronic ambulatory peritoneal dialysis (CAPD) (Iglehart, *N. Engl. J. Med.* 328:366–371, 1993; Excerpts from United States Renal Data System 1991 Annual Data Report. *Am. J. Kidney Diseases* 18(5) Supplement 2:21–30, Nov., 1991). Conventional hemodialysis for ESRD mimics to some extent the filtration function of the kidney by circulating a patient's blood through or over a dialysate solution physically separated from the blood by a porous or permeable wall or membrane. The process results in the preferential diffusion of small molecules, such as urea, from the bloodstream into the dialysate solution. Examples of some hemodialyzers and their function are described in U.S. Pat. Nos. 3,370,710; 3,373,876; 3,505.686; 3,704,223; 3,864,259; 3,884,808; 4,176,069 and 4,354,933, all incorporated herein by reference.

Although hemodialysis adequately removes small molecules from the bloodstream, no method has been established which provides for selectively removing or retaining larger molecules. Furthermore, dialysate solutions must be carefully controlled to ensure that their concentrations of biologically essential materials (such as inorganic salts and glucose) are balanced so that these materials which are present in the blood are retained by the blood. There is a strong need for a solution to these severe drawbacks.

The development of synthetic membranes with high hydraulic permeability and solute retention properties in convenient hollow fiber form has promoted ESRD therapy based upon convective hemofiltration rather than diffusive hemodialysis (Colton et al., *J. Lab. Clin. Med.* 85:355–371, 1975; Henderson et al., *J. Lab. Clin. Med.* 85:372–391, 1975; all incorporated herein by reference). Removal of uremic toxins by the convective process has several distinct advantages over diffusion. Convection imitates the glomerular process of toxin removal by providing increased clearance or passage of desirable higher molecular weight molecules and the removal of all unwanted solutes (up to a particular molecular weight cutoff) at the same rate.

Although dialysis has dramatically changed the prognosis of renal failure, it is not a complete replacement therapy, since it only provides filtration function (usually on an intermittent basis) and does not replace the homeostatic, regulatory, and endocrine functions of the kidney. Further, because dialysis functions in a nonphysiologic manner, patients with ESRD on dialysis continue to have major medical problems. The current number of patients with ESRD receiving chronic dialytic therapy in the U.S. is approximately 190,000 with the current growth rate of new patients at 8–9%. A long-term replacement therapy which replaces all of the functions of the kidney and which is less costly than current dialysis therapies is desirable.

In designing a better long-term renal replacement therapy, such as an implantable bioartificial kidney, the essential filtration and regulatory functions of kidney tissue must be developed. Some progress towards such a device has been achieved clinically with the use of polysulphone hollow fibers ex vivo which have been demonstrated to maintain the ultrafiltration function of the kidney in humans for several weeks (Kramer et al., *Klin Wochenschr* 55:1121–1122, 1977; Golper, T. A. Am. J. *Kidney Diseases* 6:373–381, 1986, both incorporated herein by reference). Limitations of this device include an increased incident of bleeding from internal or external sites of the patient due to the required anticoagulation to maintain hollow fiber patency, diminution of filtration rate due to protein deposition in the fiber over time, and the large amounts of fluid required to replace the ultrafiltrate which is removed from the blood by the filtering device and also contains useful biological material.

The use of endothelial cells seeded on the interior of the fiber conduits and filtration surfaces has been suggested as a means to provide improved long-term compatibility in vivo (Shepard et al., *Surgery* 99:318–325, 986; Kadletz et al., *J. Thorac. Cardiovasc. Surg.* 104:73642, 1992; Schneider et al., *Surgery* 103:456–462, 1988; all incorporated herein by reference). In this regard, endothelial cell seeding of a small caliber vascular prosthesis has been shown experimentally to reduce long-term platelet deposition, thrombus formation and loss of graft patency (Shepard et al., supra). These constructs have been used solely as vascular conduits and not as filtering devices.

An implantable epithelial cell system derived from cells grown as confluent monolayers along the luminal surface of impermeable polymeric hollow fibers has also been described as a first step for tubule functional replacement (Ip and Aebischer, Artificial Organs 13.:58–65, 1989, incorporated herein by reference). Critical to development of functional renal tissue is the isolation and growth in vitro of specific cells from adult kidney which possess stem cell-like characteristics such that they exhibit a high capacity for self renewal and the ability to differentiate under defined conditions into specialized cells having the correct structure and functional components of a physiologic kidney (Hall and Watt, *Development* 106:619–633, 1989; Potten and Loeffler, *Development* 110:1001–1020, 1990; Garlick et al., *J. Invest. Dermatol.* 97(5):824–829, 1991; all incorporated herein by reference). Recently, methodology to isolate and grow renal proximal tubule stem or progenitor cells from adult mammalian kidneys has been demonstrated (Humes and Cieslinski, *Exp. Cell Res.* 201:8–15, 1992; incorporated herein by reference). Alternatively, renal proximal tubule stem or progenitor cells can be isolated with electromagnetic cell sorting (Whitesides et al., *Trends in Biotechnology* 1:144–148, 1983; Padmanabhan et al., Analytical Biochem. 170:341–348, 1988; Spangrude et al., Science 241:58–62, 1988) or cell sorting based upon the density of various cell surface membrane proteins, such as integrins (see Jones et al., *Cell* 73: 713–724, 1993).

Non-serum containing growth conditions were identified which select for proximal tubule cells with a high capacity for self renewal and an ability to differentiate phenotypically, collectively and individually, into proximal tubule structures in collagen gels. Genetic marking of the cells with a recombinant retrovirus containing the lac-Z gene and dilution analysis demonstrated that in vitro tubulogenesis arose from clonal expansion of a single genetically tagged progenitor cell. Thus, a population of proximal tubule cells resides within the adult kidney which exists in a relatively dormant, slowly replicative state, but which retains a rapid potential to proliferate, differentiate and undergo pattern formation to regenerate the proximal tubule epithelium of the lining of the kidney following severe ischemic or toxic injury.

Ex vivo studies on these renal proximal tubule progenitor cells have demonstrated that the growth factors, TGF-β and EGF, along with retinoic acid, can promote differentiation of these cells into renal tubules (Humes and Cieslinski, *Exp. Cell Res.* 201:8–15, 1992). Thus, a coordinated interplay between growth factors and retinoids appears to be required to induce pattern formation and morphogenesis. In addition, using immunofluorescence microscopy, it has also been demonstrated that retinoic acid induces laminin A and $B_1$ chain production in these cells and that purified soluble laminin can be completely substituted for retinoic acid in kidney tubulogenesis (Humes and Cielinski, supra). Retinoic acid, as a morphogen, appears to promote pattern formation and differentiation by regulating the production of an extracellular matrix molecule.

Renal tubule epithelial cells have been demonstrated to maintain the differentiated transport functions of the specific nephron segments from which they were derived (Burg et al., *Am. J. Physiology* 242:C229–C233, 1982; Steele et al., *Am. J. Physiology* C136–C139, 1986; Amsler et al., *Ann. N.Y. Acad. Sci.* 456:420–435, 1985; Husted et al., Am. J. Physiology 250:C214–C221, 1986; Bello-Reuss et al., Am. J. Physiology 252:F899–F909, 1987; Blackburn et al., *Kidney International* 33:508–516, 1988). These references are incorporated herein by reference.

An implantable bioartificial renal device, which can replace renal function and as a result can circumvent the need for long-term dialytic therapy, would substantially benefit patients suffering from ESRD by increasing life expectancy, increasing mobility and flexibility, increasing quality of life, decreasing the risk of infection, and reducing therapy costs.

SUMMARY OF THE INVENTION

Accordingly one object of the present invention is to provide bioartificial devices to replace renal function in patients with acute renal failure or chronic end stage renal disease. In particular embodiments of the present invention, these devices include a filtration device and a tubule processing device. All of the devices, in singular or in combination, can be used ex vivo (attached to, and coordinated with the blood flow of, the body) or may be fully implanted in vivo. Alternatively, a bioartificial kidney is provided which comprises a filtration device followed in series by, or used in parallel with, a tubule processing device.

On the basis of these findings and other findings described below, the present invention provides (1) an implantable bioartificial filtration device which performs in vivo the function of the glomerulus and (2) an implantable bioartificial tubule processing device which performs in vivo the function of the kidney tubules. These two devices can be used either independently or in conjunction with each other. When they are used in conjunction with each other the two devices can be used independently ex vivo or in vivo.

The bioartificial devices according to the present invention combine hollow fiber technology with renal cell technology. Porous hollow fibers are membranes that allow molecular exchange analogous to exchange across capillary membranes. The pore size can be controlled in the manufacturing process. A single hollow fiber or bundle thereof can be potted within a shell or cartridge. This provides two spaces: a luminal space within the hollow fiber and a space surrounding the hollow fiber but within the shell. Depending on the type of cells seeded within these devices, various biological functions can be reproduced.

BRIEF DESCRIPTION OF THE FIGURES

FIG. 1 contains phase contrast micrographs of adult rabbit renal proximal tubule cells which were grown ex vivo in primary cultures with EGF and RA (no TGF-β).

DETAILED DESCRIPTION OF THE PREFERRED EMBODIMENTS

The present inventors have found that a population of cells resides in the adult kidney which has retained the capacity to proliferate and morphogenically differentiate into tubule structures in vitro. These cells retain a high capacity for self renewal and an ability to differentiate phenotypically, collectively and individually, into proximal tubule structures. The inventors have identified non-serum containing growth conditions that select for these proximal tubule cells. The present inventors have discovered that the growth factors, TGF-$\beta$1 and EGF, or alternatively TGF-$\beta$1 and TGF-$\alpha$, along with a retinoid, retinoic acid (RA), promoted tubulogenesis in renal proximal tubule progenitor cells in tissue culture. The inventors have now found that tubulogenesis can be induced in three dimensional collagen gels with RA and EGF.

Figure 1A:
FIG. 1a illustrates monolayers of cells on a three-dimensional collagen gel.
Figure 1B:
FIG. 1b illustrates aggregates of tubule cells.
Figure 1C:
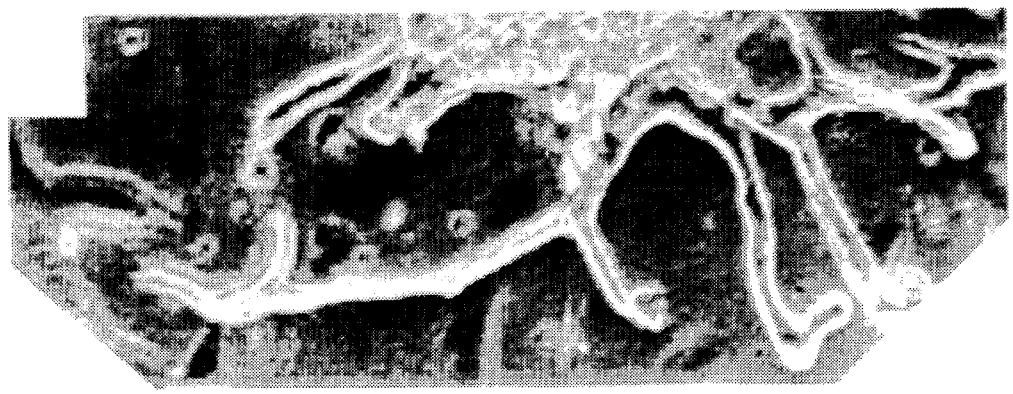
FIG. 1c illustrates long branching tubule structures.

Under selective serum-free growth conditions which included epidermal growth factor and retinoic acid, a subpopulation of renal proximal tubule cells isolated from adult rabbit kidney can be grown in cell culture. These cells possess two important characteristics: (i) an ability to differentiate morphogenically into tubule structures when grown in three-dimensional collagen gels, and (ii) a high capacity for self renewal. Cell lineage analysis with a recombinant retrovirus has demonstrated that in vitro tubulogenesis arose from clonal expansion of a single cell. Retinoic acid (RA) and epidermal growth factor (EGF) were chosen for three reasons. First, previous work with skin keritinocytes in tissue culture suggested that cells with stem cell-like characteristics were enriched in cell culture when grown in conditions which induced premature terminal differentiation (Rogers et al., *J. Cell Biol.* 110: 1767–1777, 1990; Parkinson et al., *Carcinogenesis* 3, 525–531, 1982). Second, RA has been demonstrated to be an effective differentiating agent in embryonic stem cells and in renal proximal tubule cells in tissue culture (Humes and Cielinski, supra; Rogers et al., supra). Third, EGF is the most potent renal proximal tubule cell mitogen presently described (Humes et al., *Lab Invest.* 64: 538–545, 1991; Parkinson, supra). Thus, the combination of a potent growth promoter, EGF, and a differentiating agent, RA, would provide positive selection pressure for cells which have a high capacity for replication and negative selection pressure for cells which are terminally differentiating. Although serial passage of renal proximal tubule cells have been difficult to achieve previously, these growth conditions with RA and EGF have resulted in an ability to grow these cells for more than 20 serial passages. The use of both RA and EGF were necessary for consistent passage of these cells. The ability of these renal tubule cells to morphologically differentiate and pattern form into tubule-like structures can be demonstrated by growing adult rabbit renal proximal tubule cells in primary culture followed by growth under selection pressure with RA and EGF for several passages. Renal tubule cells grown under this selection condition can then be dispersed to prepare a single cell preparation, suspended in three-dimensional collagen gels and grown in serum-free, hormonally defined culture media supplemented with RA and EGF for 7 to 14 days (suitable procedure are described in Yang et al., *Proc. Natl. Acad. Sci. U.S.A*, 76: 3401–3405, 1979; Bennett, *Nature* 285: 657–659, 1980; Montesano et al., *Cell* 42: 469–477, 1985, the texts of which are incorporated herein by reference). Within several days, cells grown under these conditions in collagen gels form luminal tubular structures as evidenced by phase contrast microscopy (FIGS 1a–1c). Progressive passage of cells promoted increasingly more defined tubular structures. Semithin sections of the collagen preparation confirm the tubular nature of the cell clusters. Cell aggregates within the collagen gel monolayers of cells in cylindrical arrays surrounding centralized lumens. Thin sections demonstrate that the lumens were bordered by polarized epithelial cells with well-defined microvilli and tight junctional complexes along the apical luminal border. A monolayer of cells also grows along the surface of the collagen gel. These surface cells possess broad based microvilli projecting into the culture medium along the apical border. Tight junctional complexes are also present between these surfaces cells near the apical border exposed to the culture medium. In either EGF, RA, or both EGF and RA in combination are omitted from the culture media, tubule-like structures within the collagen gel do not form. Thus, both EGF and RA must be present in the growth media for renal proximal tubule cells to pattern form into tubules with a differentiated, polarized epithelial cell phenotype in vitro.

Thus, the inventors have defined a coordinated interplay between growth factors and retinoids which induce pattern formation and morphogenesis; thus defining for the first time the various inductive factors which are necessary to produce fully differentiated kidney tubules and which can be important in the organogenesis of a mammalian organ.

In addition, using immunofluorescence microscopy, retinoic acid induced the production of laminin A and $B_1$ chain in these cells. This demonstrates that the substitution of purified soluble laminin for retinoic acid can also induce kidney tubulogenesis. Thus, various insoluble factors whose biosynthesis are dependent upon EGF, TGF-$\beta$1, TGF-$\alpha$ or RA can act as morphogens to promote pattern formation and differentiation.

Further the present inventors have discovered that endothelial and epithelial cells can be grown in tissue culture, seeded into the lumen of or onto the exterior surface of semi-permeable polysulphone hollow fibers and grown to confluence, to provide a monolayer along the surface of the fiber. These fibers differ from earlier reports of cell lined conduits in both the identity and function of the cells and the permeability of the conduits.

Filtration Device

The filtration device according to the present invention comprises a device for purifying blood and suitably comprises either a single semipermeable hollow fiber or a collection of semipermeable hollow fibers in which are coated, either externally or internally, with a layer of extracellular matrix (ECM) upon which either may or may not be grown a confluent monolayer of epithelial and/or endothelial cells. Alternatively, the cells or matrix may be incorporated directly within or on the polymeric structure of the semi-permeable hollow fiber during manufacture (as described hereinafter).

The filtration device of the present invention promotes ultrafiltration of blood via convective transport of water and solutes out of the blood and across the wall of a semipermeable hollow fiber with high hydraulic permeability. Filtration of blood by a convective process has several distinct advantages: it imitates the glomerular process of toxin removal with increased clearance of higher molecular weight solutes and removes all solutes up to a selected molecular weight cutoff at the same rate. Convective transport occurs independently of the existing concentration gradient and depends predominantly on the hydraulic pressure gradient across the membrane.

Figure 2A:
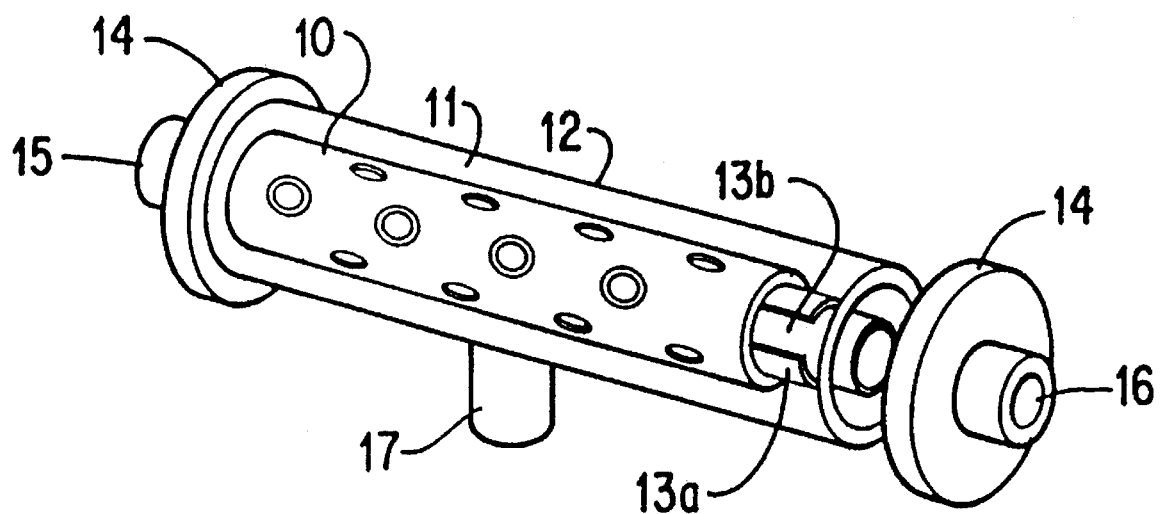
FIGS. 2a–b are schematics of two embodiments of a filtration device composed of a single hollow fiber.

In one embodiment of the invention, FIG. 2a illustrates a filtration device comprising a single hollow fiber 10 in a chamber 11 defined by a housing 12. The hollow fiber 10 is internally coated with various extracellular matrix components 13a upon which is grown a confluent monolayer comprising endothelial and/or epithelial cells 13b. Both ends of the hollow fiber 10 are cut flush to access the internal compartment of the hollow fiber. The hollow fiber 10 is then snugly fit against headers 14 using any known techniques, for example potted at both ends with potting material. Perfusion inlet port 15 and perfusion outlet port 16 are connected to the headers 14 at opposite ends. The housing is further elaborated with filtrate outlet port 17.

Blood containing undesirable impurities such as metabolic waste flows from the patient's arterial lumen, enters perfusion inlet port 15, passes through hollow fiber 10, exits through perfusion outlet port 16, whereupon it is reabsorbed into the vascular venous flow. As blood passes through the fiber, filtrate proceeds through confluent monolayer 13b, extracellular matrix 13a and the wall of hollow fiber 10, into the collecting chamber 11. Filtrate exits collecting chamber 11 through filtrate outlet port 17.

In a preferred configuration of this embodiment, the filtration device comprises a hollow fiber which is internally coated with a confluent monolayer of autologous endothelial cells. Anticoagulants are suitably introduced into the blood within the filtration unit. Suitable anticoagulants include potent thrombin inhibitors such as hirudin, hirulogs and fragments thereof which retain anticoagulant activity. To date, there are about 12 variants of hirudin, as well as hirudin fragments and hirulog compounds (Maraganore et al., *J. Biol. Chem.* 264; 8692–8698, 1989; Scharf et al., *FEBS* 255; 105–110, 1989; Maraganore et al., *Biochemistry* 29; 7095–7101, 1990). Suitable hirudin fragments useful in this embodiment include fragments which contain the catalytic site of hirudin, which blocks platelet aggregation, as well as the fibrinogen binding site, which blocks activation of coagulation (Maraganore et al., 1989, *supra*; Maraganore et al., 1990, supra; Borbon et al., *FEBS* 294:163–166, 1991).

Hirudin is a potent anticoagulant due to its potent thrombin inhibitory effect. It is a family of polypeptide chain proteins containing 64–66 residues isolated from the bloodsucking leech, *Hirudo medicinalis*. The anti-thrombin activity of hirudin is due to a tight complex formation between this protein and the enzyme to inhibit thrombin activity with a dissociation constant of 20 fM. Other similar thrombin inhibitors have been isolated from other leeches, most recently haemadin from the Indian leech, *Haemadipsa sylvestris* (Strube et al., *J. Biol. Chem.* 268:8590–8595, 1993). The cDNAs of both hirudins and haemadin have been obtained and recombinant proteins produced from expression vectors have demonstrated potent anticoagulation properties in vitro and in vivo (Maraganore et al, 1989, *supra*; Fenton, J. In *Coagulation Disorders* I 6:1121–1129, 1992; Strube et al., *supra*; Kaiser, B. *Seminars in Thrombosis and Hemostasis* 17: 130–136, 1993).

These anticoagulants can suitably be introduced via exogenous administration via subcutaneous infusion port connected to the internal compartments of the hollow fibers. Alternatively, the semipermeable fibers can be internally coated with a layer of immobilized anticoagulant compounds, preferably peptides. These compounds can either be absorbed onto the polymer or covalently attached to the polymer using conventional techniques (Andrade et al., Adv. *Polymer Sci.* 79:1–63, 1986; Lin et al., *Biomaterials* 13:905–913, 1992; Hubbel et al., *Biotechnology* 9:568–572, 1991). Covalently attached anticoagulent peptides can serve the additional function of increasing endothelial cell adhesion to the semipermeable fiber (Lin et al., *supra*; Hubbell et al, *supra*).

Alternatively, endothelial cells can be-transfected with various genes which encode these compounds (Flugelman et al., *Circulation* Research 70:348–354, 1992; Dichek et al., *Circulation* 80:1347–1353, 1989). In a preferred embodiment, the endothelial cells internally lining the fiber are transfected with cDNA encoding for hirudin or hirulog compounds and express these compounds either on the external surface of their membranes or secrete these compounds. DNA from synthesized oligonucleotides and polymerase chain reaction techniques can be obtained and code for these types of derivatives. Using this cDNA stable gene transfection with these oligonucleotides can be used to induce local production of anticoagulants along the lining layer of endothelium. Stable gene transfection with vectors containing these oligonucleotides can be achieved with conventional methods (Sambrook et al., "Molecular Cloning: A Laboratory Manual", 2nd ed. Vols 1–3, Cold Spring Harbor Laboratory, N.Y., 1989). DEAE dextrin can be used to improve transfection of DNA encoding hirudin as described by (Dichek et al, *Blood* 77:533–541, 1991; Jaklitsch et al., *J. Cell Physiol.* 154:207–216, 1993). Preferably, transfection is achieved using recombinant retroviruses. In order to ensure that hirudin, hirulogs, or hirudin fragments will be secreted from the cell, a signal peptide appropriate for secretion and cleavage or membrane binding peptide is preferably incorporated into the vectors. In an alternate preferred embodiment, the filtration device can contain both nontransduced and transfected endothelial cells.

Figure 2B:
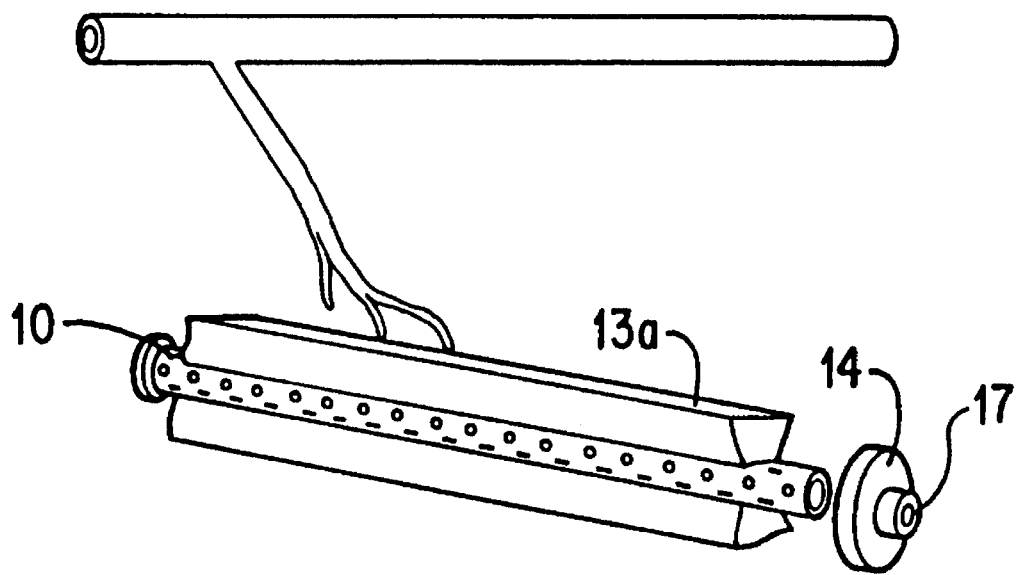

Another embodiment of the filtration device according to the present invention is illustrated in FIG. 2b. The filtration device comprises a single hollow fiber 10 defined by extracellular matrix material 13a. One end of hollow fiber 10 is cut flush so that the resulting access to the lumen of hollow fiber can be attached to filtrate outlet port 17 attached to a header 14. The opposite end of hollow fiber 10 is sealed.

Ultrafiltrate leaks from the arterial capillary lumina that are in proximity to hollow fiber 10, passes through the wall of hollow fiber 10, into the lumen of hollow fiber 10, and exits through filtrate outlet port 17.

Figure 3A:
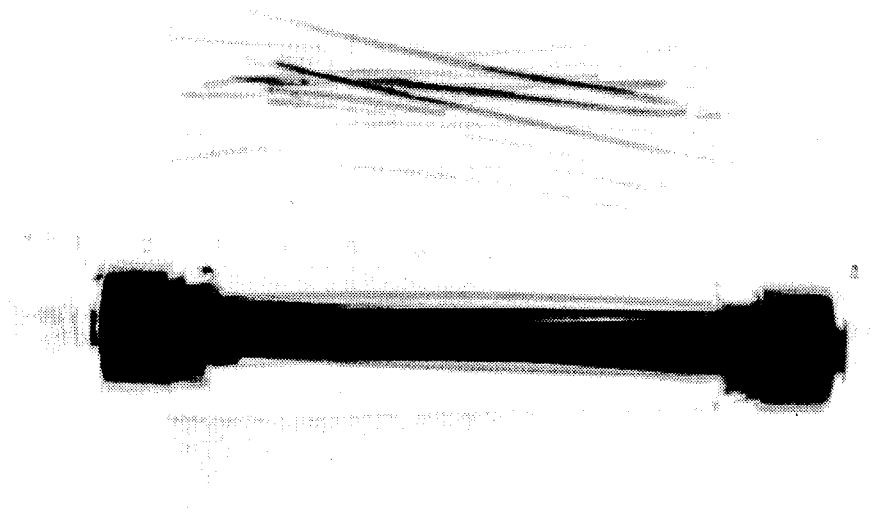
FIGS. 3a–b are photographs of two embodiments of a filtration device composed of bundles of hollow fibers.
Figure 3B:
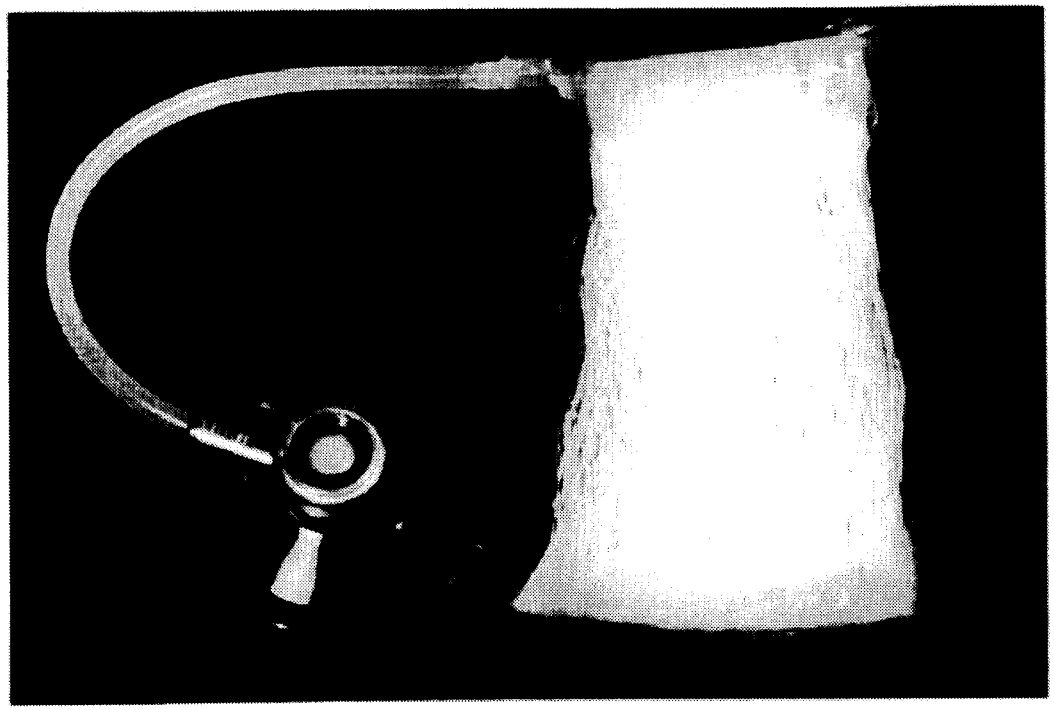

The filtration device is preferably composed of a large number of hollow fibers bundled together (FIG. 3a–b). This arrangement improves the surface area available for capillary interface with the hollow fiber bundle. In one embodiment (FIG. 3a), the hollow fibers 10 are assembled as a cylindrical array with any number of hollow fibers, preferably approximately 500 hollow fibers, measuring any suitable length, such as from 1–100 in length, being fixed, e.g., potted with potting material, on both ends. The fluid flows from the capillary lumen from the capillary lumen through the capillary wall, through the walls of the hollow fibers 10, through the walls of the fibers, into the lumen of the hollow fibers, and exits through filtrate outlet port 17.

In another preferred embodiment of the present invention (FIG. 3b), the hollow fibers are assembled as a plate with any number of hollow fibers having the same length, preferably approximately 500 hollow fibers, measuring any suitable length, such as from 1–100 in length, being fixed, for example, with potting material on both ends. One end of each fiber in the bundle is sealed and the opposite end connected to filtrate outlet port. Ultrafiltrate leaks from the arterial capillary lumina that are in proximity to hollow fiber 10, through the wall of hollow fiber 10, into the lumen of hollow fiber 10, and exits through the filtrate outlet port.

Suitable semipermeable hollow fibers useful in accordance with the present invention can be composed of any known biocompatible polymer including CUPROPHAN (a cellulose regenerated by means of the cuprammonium process, available from Enka), HEMOPHAN (a modified CUPROPHAN with improved biocompatibility, available from Enka), CUPRAMMONIUM RAYON (a variety of CUPROPHAN, available from Asahi), BIOMEMBRANE (cuprammonium rayon available from Asahi), saponified cellulose acetate (such as fibers available from Teijin or CD Medical), cellulose acetate (such as fibers available from Toyobo (Nipro), cellulose (such as those regenerated by the modified cupramonium process or by means of the viscose process, available from Terumo or Textikombinat (Pirna, GDR) respectively), polyacrylonitrile (PAN), polysulphone, acrylic copolymers (such as acrylonitrile-NA-methallyl-sulfonate copolymer, available from Hospal), polycarbonate copolymer (such as GAMBRONE, a fiber available from Gambro), polymethylmethacrylate copolymers (such as fibers available from Toray) and ethylene vinyl copolymer (such as EVAL, a ethylene-vinyl alcohol copolymer available from Kuraray). Preferably, polysulphone fibers are used. Other suitable biocompatible fibers are disclosed by Salem and Mujais, In *Dialysis Therapy*, ch. 5, 2nd ed., Nissenson and Fine, Eds., Hanley & Belfus, Inc., Pennsylvania, 1993.

The hollow fibers must have high hydraulic conductivity, as measured in terms of the ultrafiltration coefficient. Suitably, the ultrafiltration coefficient is greater than 20 mL/hr, Torr, $m^2$ preferably 20–100 mL/hr,Torr, $m^2$. The hollow fibers suitably have a molecular weight cutoff, or pore size, which is less than or equal to 60,000 g/mol.

Figure 4:
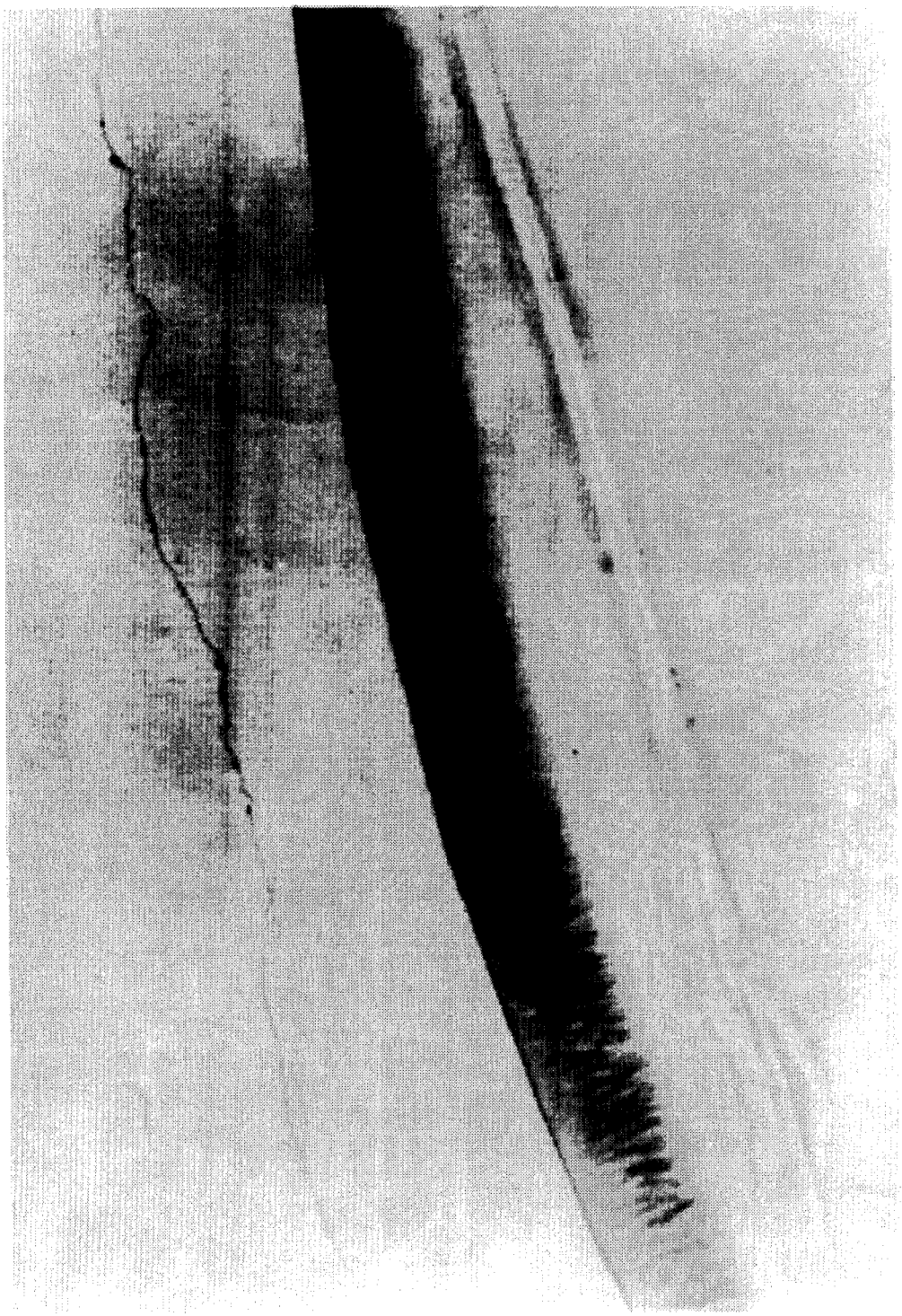
FIG. 4 is a light micrograph of a polysulfone hollow fiber internally seeded with a layer of collagen type I along its inner surface.
Figure 5A:
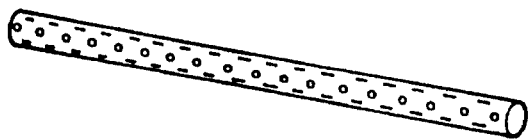
FIG. 5 is a schematic representation of a vascular infiltration of a bundle of hollow fibers.
Figure 5B:
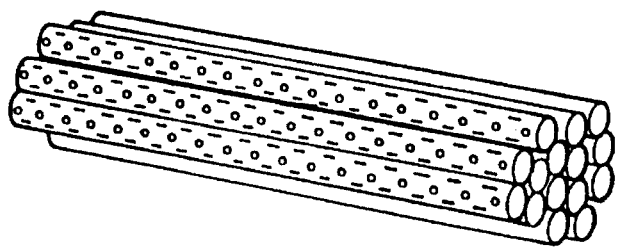
Figure 5C:
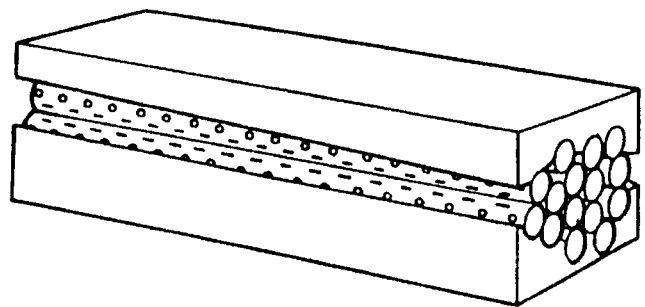
Figure 5D:
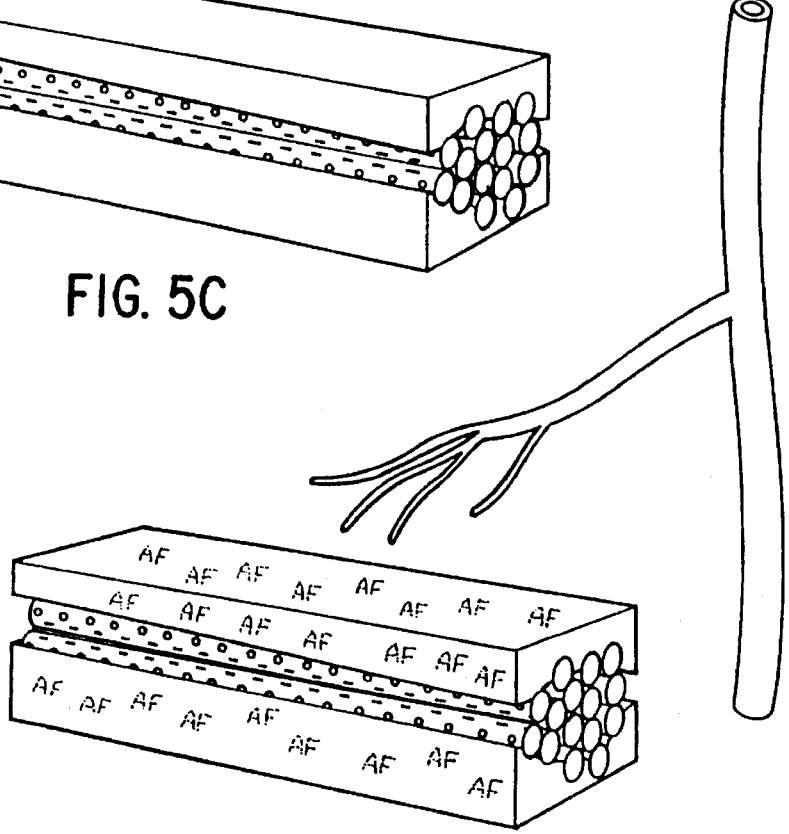

The internal and/or external surface of the hollow fiber is precoated with suitable extracellular matrix (ECM) components including Type I collagen, Type IV collagen, laminin, Matrigel, proteoglycan (such as heparin sulfate and dermatan sulfate) fibronectin, and combinations thereof to form an ECM layer. FIG. 4 is a light micrograph of an illustrative polysulfone hollow fiber lined with a layer of collagen type I along its inner surface. In this figure, the fiber is seen with the outer contour of the hollow fiber identified by an irregular line at the top. The collagen layer is at the bottom and stains darker with a fibrillar appearance. Lower power examination (not shown) demonstrates a smooth layer of collagen along the entire circumference of the inner surface of the hollow fiber.

Once an ECM layer has been established on the surface(s) of the hollow fiber, this layer is then seeded with endothelial cells. Endothelial cells according to the present invention can be cultured using known techniques. Suitably endothelial cells are autologous cells isolated from the patient. Harvested cells are seeded into each hollow fiber contained within the filtration device. The cells are then cultured on the ECM layer until a confluent monolayer is established along the interior of the hollow fiber. Suitable culturing techniques useful for seeding these cells on the surface of the fiber are described by Scott et al., *J. Cell Sci.* 105:269–273, 1993; Schneider et al., *Surgery* 103:456–462, 1988; Kadletz et al., *J. Thoracic and Cardiovascular Surgery* 104:736–742,1 1992; Shepard et al., *Surgery* 99: 318–326, 1986; and Demetriou et al., *Science* 23:1190–1192, 1986.

Suitable potting material useful for attaching the semipermeable hollow fibers into the chamber of the filtration device include polyurethane, silicon or any elastomeric substance which is biocompatible.

The remaining elements of the device may be made of any known biocompatible material(s).

The filtration device can be suitably implanted either subcutaneously, on the peritoneal membrane, or within various tissues (such as muscle or kidney). Alternatively, the filtration device may be located outside the body.

Site directed neovascularization can then be promoted with suitable angiogenic factors and soluble factors (see FIG. 5). Angiogenesis is the formation of blood vessels in situ and involves the orderly migration, proliferation, and differentiation of vascular cells. The initiation of angiogenesis by direct formulation of endothelial cell proliferation is the presumed responsibility of polypeptide mitogens: acidic fibroblast growth factor, basic fibroblast growth factor, fibroblast growth factor-5, hepatocyte growth factor and vascular endothelial growth factor. These polypeptides have been shown to be mitogens for endothelial cells in vitro and angiogenesis in vivo (Thompson et al., *Science* 242:1349, 1988).

In this embodiment (corresponding to the second embodiment discussed hereinbefore), the hollow fibers act as collecting conduits of ultrafiltrate produced by the newly-formed capillary network induced by the angiogenic factors. This formulation is based upon the intrinsic property inherent in all capillary beds to produce ultrafiltrate. This filtrate, or transudate, will collect in the hollow fiber network rather than the usual physiologic sites consisting of the interstitial space and lymphatics. The vectorial filtrate flow will be from capillary through the interstitium into the hollow fiber(s), since the hydraulic pressure difference from capillary lumen to hollow fiber(s) will be greater than 20 mm Hg when the hollow fiber system is connected to its external drainage and collection system. Soluble and insoluble factors, as well as the angiogenic substances, can be supplied to the area surrounding the hollow fibers to maintain and increase capillary density.

Suitable angiogenic factors useful in accordance with the invention include: FGF-5, FGF-1, FGF-2, hepatocyte growth factor, vascular endothelial growth factor, etc. Suitable insoluble factors useful in accordance with the present invention include: complex extracellular matrices, such as collagen gels or Matrigel, or purified extracellular matrix molecules, including laminin, fibronectin, collagen types I and IV, etc.

Suitable soluble factors useful in accordance with the present invention include: growth promoters, such as fibroblastic growth factor, and growth inhibitors, including TGF-β.

The source of the above identified factors can be either from exogenous administration via a subcutaneous infusion port connected to the internal compartments of the hollow fibers.

In another embodiment of the present invention, living cells are co-extruded in the core of a hollow fiber as it is spun. This methodology has been described by Aebischer et al. in *Exp. Neurology* 111:269–275, 1991, incorporated herein by reference. This technology can also be extended to establish a layer of, or to covalently link, ECM components to the inner surface of the hollow fiber as it is formed by a spinerette assembly. The cells are then extruded onto this matrix material (Aebischer et al., *supra*; Lin et al., *Biomaterials* 12:905, 1992). Thus, mass bulk production of hollow fibers layered internally with ECM components and cells can be achieved. The hollow fibers can then be bundled, potted, and cut at both ends, then encased in plastic with input and output ports connected to headers attached to each of the potted ends of the hollow fiber cartridge. This cartridge can then be placed in a bioreactor for growth to confluency.

Tubule Processing Device

Figure 6A:
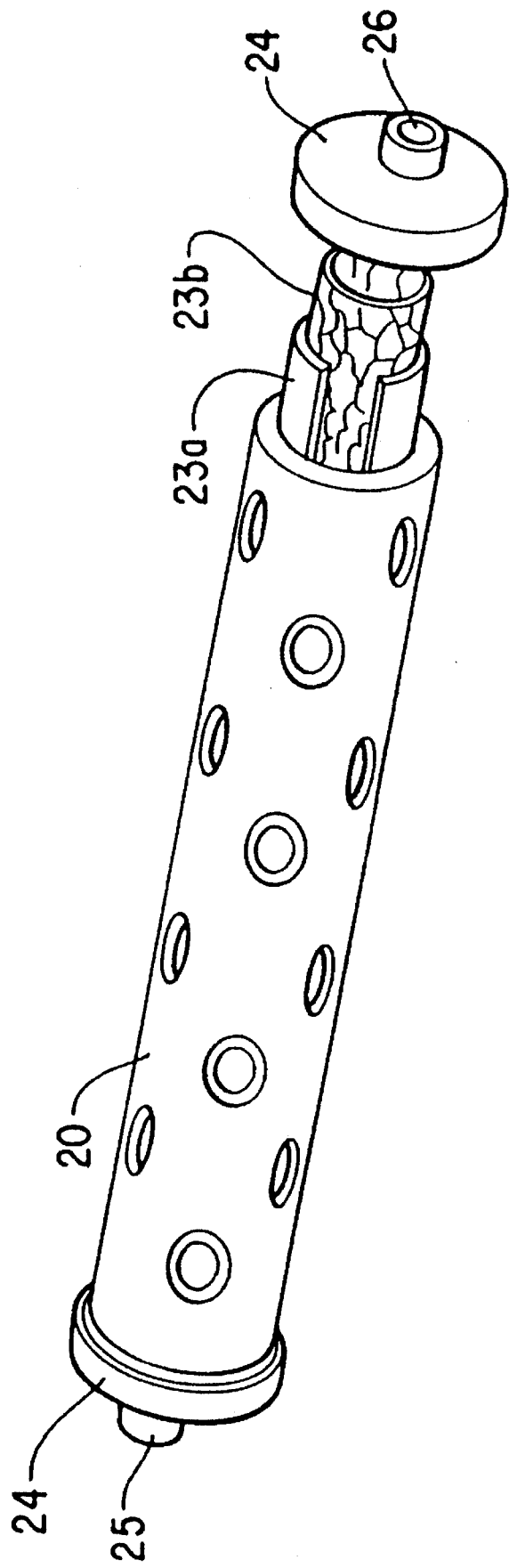
FIGS. 6a–b are schematic representations of a tubule processing device composed of a hollow fiber seeded, respectively, internally and externally with differentiated renal tubule cells.

A first embodiment of the tubule processing device according to the present invention comprises a single hollow fiber seeded with living renal tubule cells on its internal surface. FIG. 6a illustrates a tubule processing device comprising a hollow fiber which is internally coated with various extracellular matrix components 23a and a confluent monolayer of renal tubule cells 23b. The hollow fiber 20 is attached at both ends to headers 24, one of which contains filtrate inlet port 25 and the other of which contains urine outlet port 26.

Filtrate flows from the filtration device described above, or any other filtration device known in the art, into the lumen of the hollow fiber 20 via filtrate inlet port 25 and exits via urine outlet port 26. Fluid is reabsorbed from the filtrate by the confluent monolayer 23b containing renal tubule cells derived from renal tubule stem or progenitor cells and is transported through the hollow fiber walls and eventually is reabsorbed into the systemic circulation. The remaining fluid which is not reabsorbed flows out of the fiber lumen and exits through the urine outlet port 26.

Figure 6B:
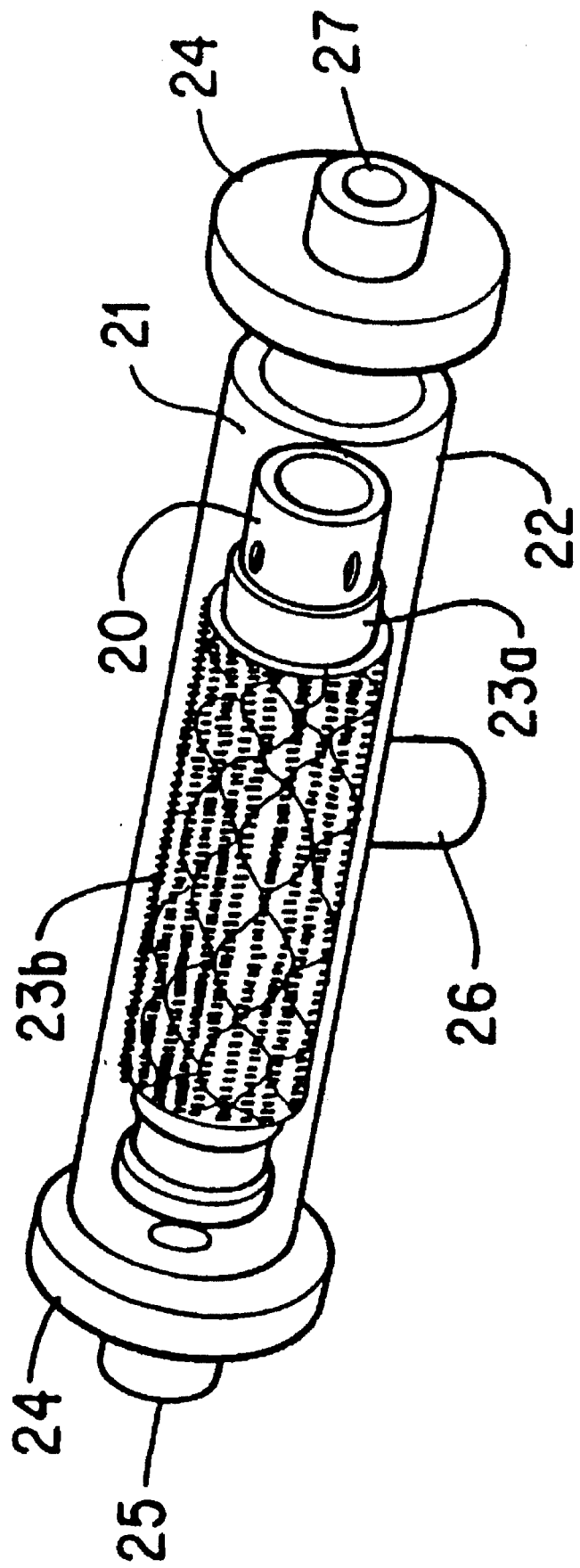

A second embodiment of the tubule processing device according to the present invention comprises a single hollow fiber seeded with living renal tubule cells on its external surface. FIG. 6b illustrates a tubule processing device comprising a chamber 21 defined by a housing 22. A single hollow fiber 20 is externally coated with various extracellular matrix components 23a and a confluent monolayer of renal tubule cells 23b. The hollow fiber 20 is attached at both ends of the chamber to headers 24, for example with potting material. One end of the hollow fiber 20 is sealed and the other end is cut flush so that the resulting access to the lumen of hollow fiber can be attached to reabsorbate outlet port 27. The housing is further elaborated with filtrate inlet port 25 and urine outlet port 26.

Filtrate flows from the filtration device into filtrate inlet port 25 and exits urine outlet port 26. Some fluid is reabsorbed from the filtrate by the renal tubules cells within the confluent monolayer 23b and is transported into the lumen of the hollow fiber. Reabsorbate flows out of the fiber via reabsorbate outlet port 27 and is delivered into systemic circulation.

A third embodiment of the tubule processing device comprises a single semipermeable hollow fiber with no extracellular matrix and no cells.

The tubule processing device is preferably composed of a large number of hollow fibers bundled together. This arrangement improves the surface area available for capillary interface with the hollow fiber bundle. In one embodiment, the hollow fibers are internally coated with a confluent monolayer of renal tubule cells. The fibers are assembled as a plate with any number of hollow fibers, preferably approximately 100–500 hollow fibers, measuring any suitable length, such as from 1–2000 cm in length, being fixed, e.g., potted with potting material, on both ends. One end of each fiber is attached to a filtrate inlet port and the opposite end is attached to a urine outlet port.

Ultrafiltrate flows into a filtrate inlet port through the hollow fibers and over the renal tubule cells. Fluid which is reabsorbed by the cells passes through the semipermeable fibers into the surrounding tissues. Ultrafiltrate which is not absorbed exits through a urine outlet port.

In a second preferred embodiment, the hollow fibers are externally coated with a confluent monolayer of renal tubule stem cells. The hollow fibers are assembled in a cylindrical array with any number of hollow fibers having the same length, preferably approximately 500 hollow fibers, measuring any suitable length, such as from 1–2000 cm in length, preferably fixed, for example, with potting material on both ends. One end of each fiber is sealed and the other end is attached to a reabsorbate outlet port. The fibers are in a chamber defined by a housing which contains blood filtrate inlet and urine outlet ports.

Ultrafiltrate enters the chamber through the blood filtrate inlet port and passes over the fibers coated with renal tubule cells. Fluid which is reabsorbed by the cells passes through the semipermeable fibers into the lumina of the fibers and exits through the reabsorbate outlet port. Ultrafiltrate which is not absorbed exits through the urine outlet port.

Suitable materials useful for constructing the semipermeable hollow fibers in the tubule processing unit according to the present invention are similar to those described above for the filtration unit. Renal proximal tubule reabsorption is based upon active $Na^+$ transport which develops a small degree of luminal hypotonicity, resulting in a transepithelial osmotic gradient to drive isotonic fluid reabsorption. Proximal tubule reabsorption is based upon a membrane system with a high diffusive water permeability, low ultrafiltration rate, and a pore size with very low molecular weight cutoff. A suitable hollow fiber cell culture module is commercially available from Cellco (Germantown, Md.) and comprises a hollow fiber cartridge based upon cellulose membranes with high diffusive water permeability, low ultrafiltration coefficient, and a pore size with molecular weight cutoff of 4,000 daltons. Alternatively, semipermeable fibers which have pore sizes which are decreased or increased in comparison to the filtration unit can be used. Preferably the pore size (or molecular weight cutoff) is no greater than about 70,000 g/mol, a pore size which prevents antibodies from penetrating into the fibers. The hydraulic pressure within the semipermeable fibers of the tubule processing unit is suitably lower than that of the filtration unit, preferably less than about 10 mmHg. The hydraulic pressure within the tubule processing unit can suitably be controlled by varying the length, size and inner diameter of the conducting conduit which attaches the filtration unit to the tubule processing unit.

The hollow fibers useful in the tubule processing device are seeded with renal tubule epithelial cells. Cells grown within the hollow fiber are immunoprotected from the bloodstream due to the impenetrance of immunologically competent cells through the hollow fiber. Rejection of transplanted cells will, therefore, not occur, in this configuration.

Epithelial renal progenitor cells are suitably obtained and cultured using conventional techniques as described in Humes et al., *Exp. Cell Res.* 201:8–15; Taub et al., *J. Biol. Chem.*, 254, 11440–11444; Taub et al., *J. Cell Physio.*, 106 191–199; Taub et al., *J. Supramol. Struct*, 11, 07–216; Taub et al., *J. Cell Physiol*, 105, 369–378; Taub et al., *Proc. Nat. Acad. Sci. U.S.A*, 79, 3338–3342; Taub et al., Ann. *New York Acad. Sci.*, 372, 406–421; Taub et al., *J. Supramol. Struct.*, 15, 63–72; and Taub et al., *J. Cell Physiol*, 114, 153–161; which are all incorporated herein by reference.

Figure 7A:
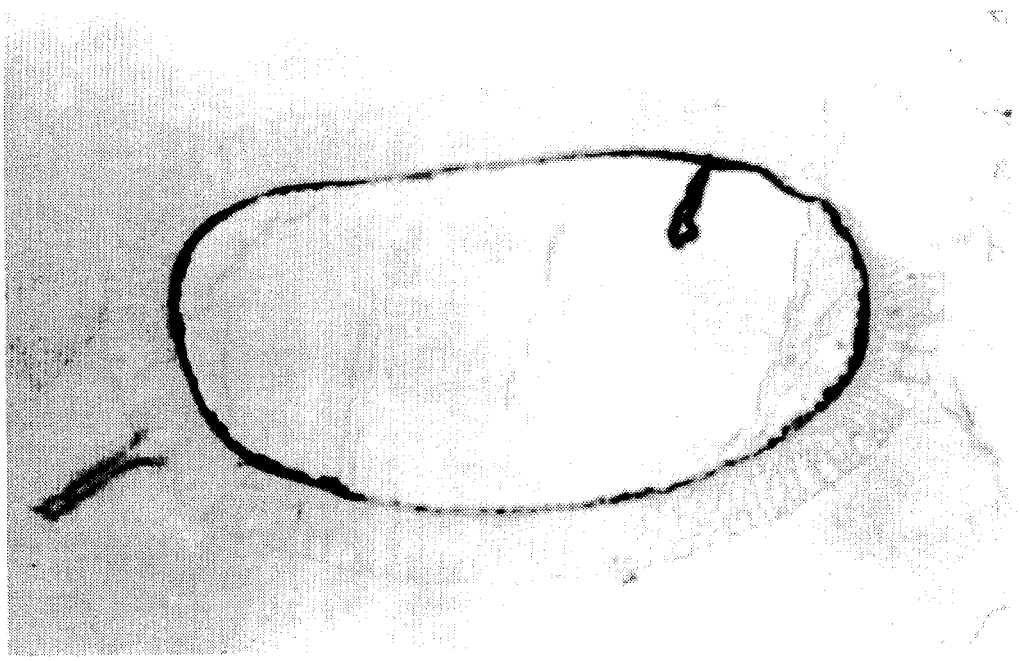
FIG. 7a is a cross sectional photograph of the hollow fiber internally seeded with epithelial cells.
Figure 7B:
FIG. 7b is a light micrograph of a polysulfone hollow fiber internally seeded with a layer of laminin and a layer of renal tubule cells with differentiated morphology along its inner surface.

Cultured cells can be seeded on water and solute-permeable membranes precoated with various biomatrix materials, so that the expression of differentiated vectorial transport, metabolic, and endocrinologic function is attained. Immunoprotection of the cultured progenitor cells is achieved concurrent with long-term functional performance as long as conditions support tubule cell viability. Cultured cells seeded on the interior of the hollow fibers are immunoprotected by the hollow fiber. Cultured cells seeded on the exterior of the hollow fiber are immunoprotected by the housing of the device. FIG. 7 is a light micrograph of an illustrative polysulfone hollow fiber lined with a layer of laminin and renal epithelial cells along its inner surface. In this figure, the fiber is seen with the outer contour of the hollow fiber identified by an irregular line at the top. The collagen layer is at the bottom and stains darker with a fibrillar appearance. Higher power examination demonstrates a smooth layer of renal epithelial cells with differentiated morphology along the entire circumference of the inner surface of the hollow fiber.

Renal proximal tubule progenitor cells can be induced to differentiate morphogenically by culturing them in hormonally-defined cultures as described by Humes and Cieslinski in Exp. *Cell Res*. 2.0:8–15, 1992, incorporated herein by reference. New data shows that differentiation of renal proximal tubule progenitor cells can be induced with EGF and RA in 3-dimensional collagen gels.

A hormonally-defined renal cell culture is treated with epidermal growth factor and all-trans retinoic acid. This treatment transforms a confluent monolayer of renal proximal tubule cells into epithelial cell aggregates containing lumens, bordered by cells with a differentiated polarized epithelial cell phenotype. If the ECM layer is either absent or not well developed, transforming growth factor-$\beta_1$ is suitably added to the culture to promote tubulogenesis.

When necessary, transforming growth factor-$\beta_1$ is suitably administered to achieve a concentration of from 0.1 ng/ml–1 mg/ml, epidermal growth factor in a concentration range of from 0.1 nM to 1 µM, and all-trans retinoic acid in a concentration range of from 0.01 µM to 100 µM.

Soluble factors can optionally be added to the renal tubule stem cell culture. Preferred soluble factors include, but are not limited to, fetal calf serum, prostagladins, hydrocortisone triiodothyronine, selenium, fibroblastic growth factor, transforming growth factor-$\alpha$, hepatocyte growth factor, and combinations thereof. These soluble factors are preferably added in the following concentrations: fetal calf serum, 3–25% (volume/volume) of growth media; prostaglandin $E_1$, 1 to 100 ng/ml; triiodothyronine, 0.1 nM to 1 µM; selenium, 0,001 to 1.00 µM; cholesterol, 1.0 nM to 0.10 µM; transferrin, 1 to 50 µg/ml; transforming growth factor-$\alpha$, 0.1 nM to 1 µM; insulin, 1–50 g/ml; hydrocortisone, 1 nm to 1 µM; and hepatocyte growth factor 0.1 ng/ml to 100 ng/ml.

Insoluble factors can additionally be added to the renal tubular stem cell culture. These insoluble factors include, but are not limited to, a variety of extracellular matrix molecules such as Type I collagen, Type IV collagen, laminin, proteoglycans, fibronectin, and combinations thereof. These insoluble factors are preferably added in the following concentrations: collagen, Type I, 1 to 5 mg/ml; collagen, Type IV, 0.01 to 5 mg/ml; laminin, 10 to 1000 µg/ml; heparin sulfate, 10 to 1000 5 g/ml; and heparin, 10 to 1000 µg/ml.

Suitable filtration rates in accordance with the present invention may be varied depending upon the need of the patient but are typically of from 10–15 ml/minute of blood through the filtration and tubule processing devices in adult humans. This filtration rate is compatible with life as proven in clinical states of renal insufficiency without dialytic support. This rate forms 14–15 liters of filtrate per day. The reabsorption rate of the tubule device is at least 50% of the amount which is presented. This rate can be adjusted by increasing the number or length of hollow fibers in the tubule processing device.

The tubule processing device is suitably implanted either subcutaneously or within the peritoneal cavity.

Bioartificial Kidney

Four embodiments of the bioartificial kidney according to the present invention are depicted in FIG. 8*a–d* and each is comprised of a filtration device, as described above, followed in series by a tubule processing device as described above. Alternatively, the bioartificial kidney comprises a conventional filtration device such as a device which provides continuous arteriovenous hemofiltration (CAVH) and which is based on convective transport (Salem and Mujais, supra; Macias et al., *Amer. J. Kidney Dis*. XVIII:451–458, 1991; "Clinical Dialysis", 1st ed., Appleton-Century-Crofts, East Norwalk, Conn., 1984; "Dialysis Therapy", 2nd ed., Hanley & Belfus, Inc., Pennsylvania, 1993) followed in series by a tubule processing device as described above. The filtrate formed in the filtration device will flow directly into the tubule processing device where biologically useful metabolic substrates and inorganic salts will be removed from the filtrate and reabsorbed into systemic circulation. After the filtrate from the filtration device is processed by the tubule processing device, the final fluid (urine) can be collected from the tubule device by tubing which is inserted into the patient's ureter to maintain a natural conduit for urine excretion from the individual. Alternatively, urine can be collected by a catheter.

Figure 8A:
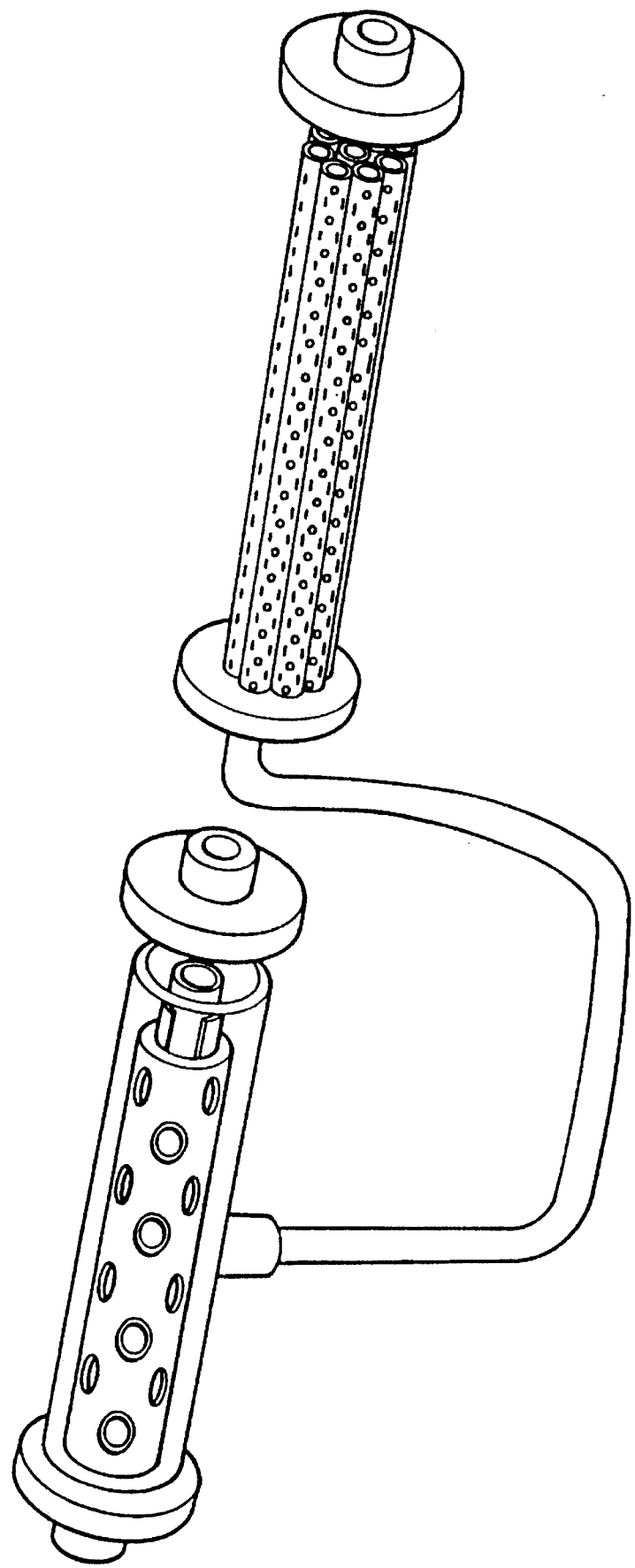
FIGS. 8a–d are a schematic representations of a bioartificial kidney comprising a filtration device followed in series by a tubule processing device.
Figure 8B:
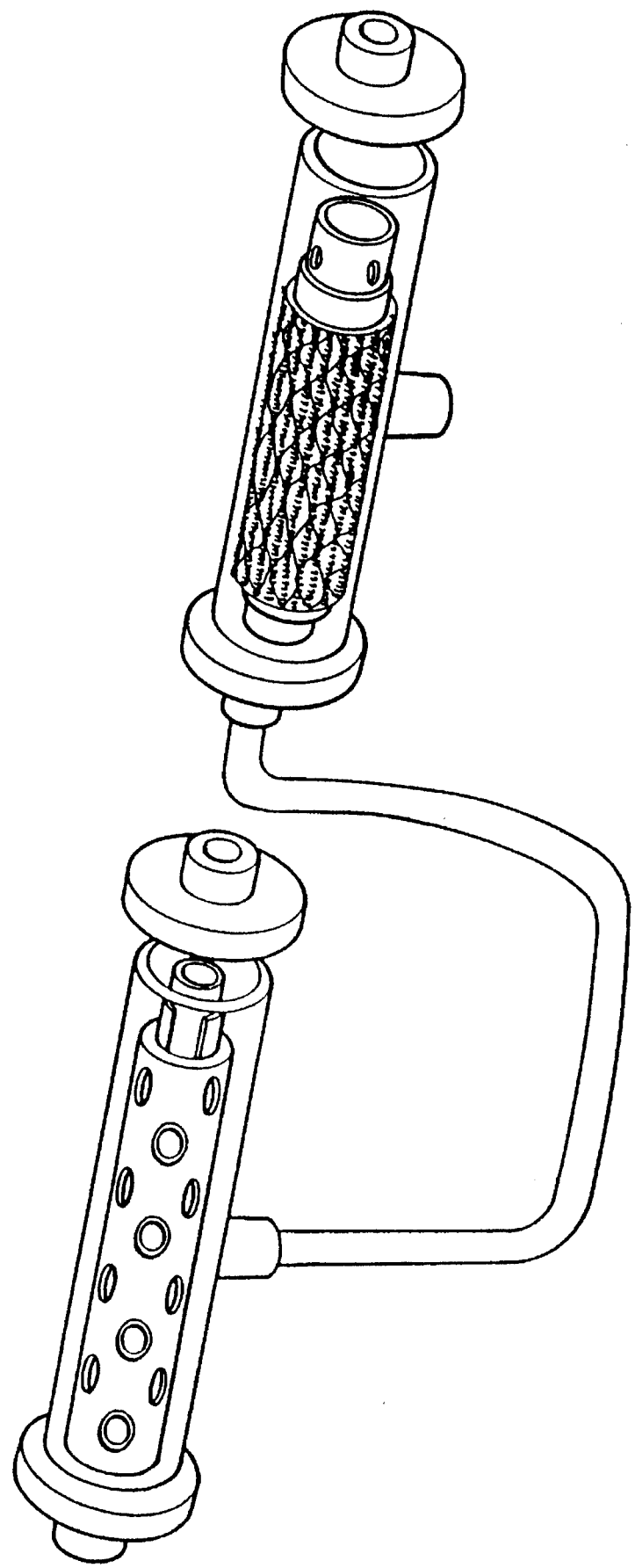
Figure 8C:
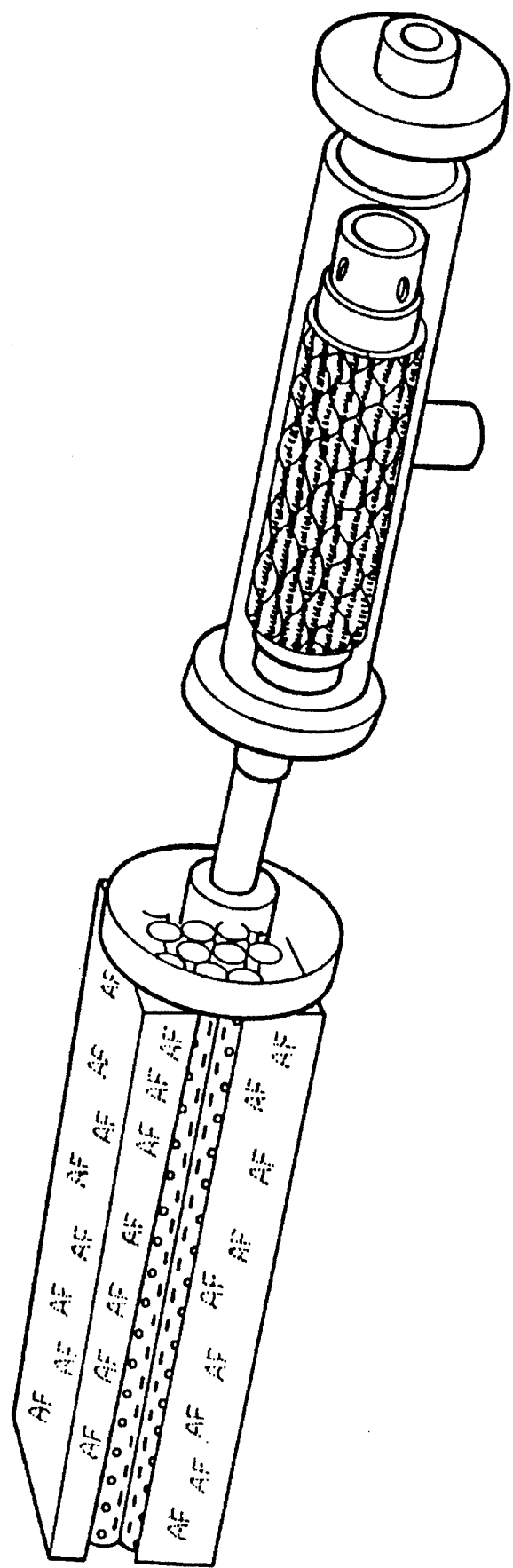
Figure 8D:
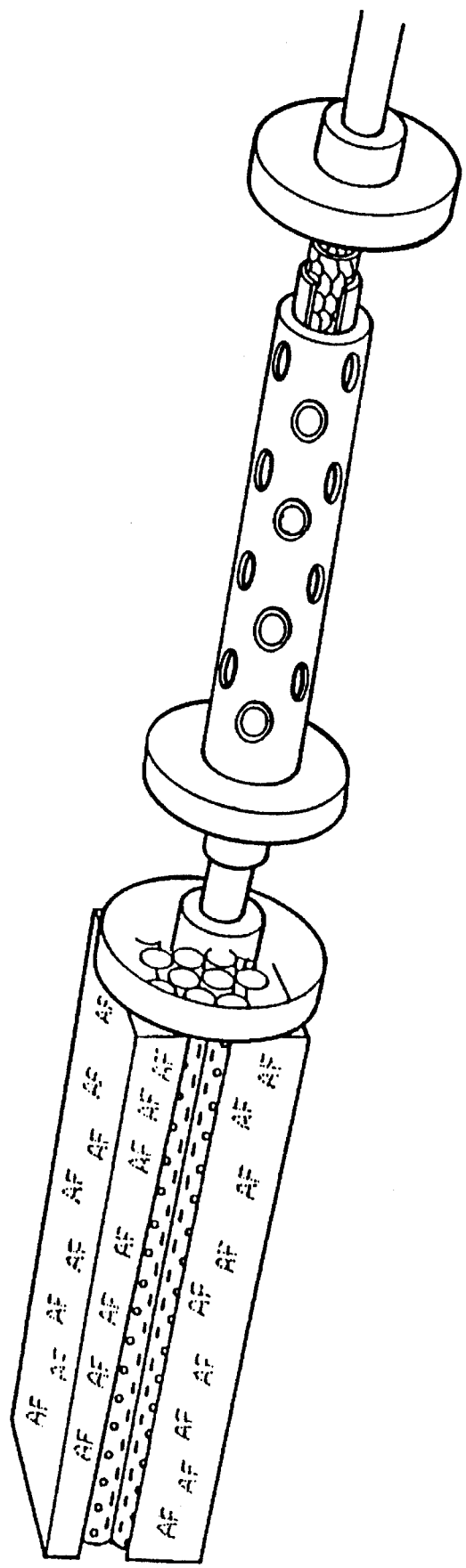
Figure 8E:
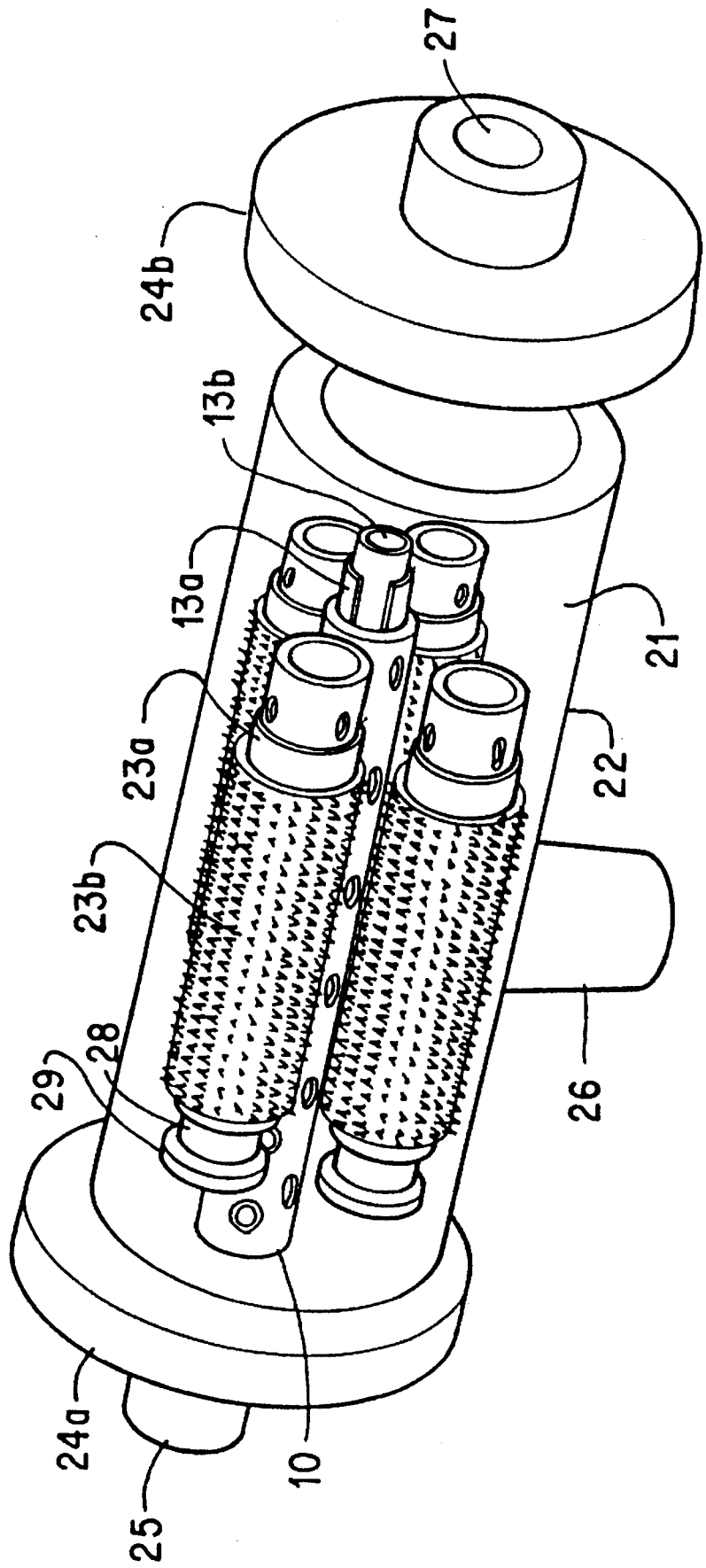
FIG. 8e is a schematic representations of a bioartificial kidney comprising a filtration device in parallel with a tubule processing device.

A fifth embodiment of the bioartificial kidney according to the present invention is depicted in FIG. 8*e* and comprises a single device composed of a plurality of two types of semipermeable hollow fibers bundled together in a cylindrical array. The hollow fibers are located in a chamber 21 defined by a housing 22. The hollow fibers are snugly fit against headers 24*a* and 24*b* using any known techniques, for example by potting both ends of said fibers with potting material. Perfusion inlet port 25 and perfusion outlet port 27 are connected to the headers at opposite ends. The housing is further elaborated with urine outlet port The first type of hollow fiber 10 is internally coated with various extracellular matrix components 13*a* and a confluent monolayer of endothelial and/or epithelial cells 13*b* (preferably endothelial cells are used). Both ends of this type of hollow fiber are cut flush to access the internal compartments of the hollow fibers. One end is attached to a perfusion inlet port 25 and the opposite end is attached to a perfusion outlet port 27.

The second type of hollow fiber 28 is externally coated with various extracellular matrix components 23*a* and a confluent monolayer of renal tubule cells 23*b*. One end of this type of hollow fiber is sealed 29 whilst the opposite end is cut flush to access the internal compartments of the hollow fiber. The resulting access to the lumen of the hollow fiber is attached to the perfusion outlet port 27.

Blood containing undesirable impurities such as metabolic waste which flows from the patient's arterial lumen, enters the perfusion inlet port, through the first type of hollow fibers, and exits through perfusion outlet port, whereupon it is reabsorbed into the vascular venous flow. As blood passes through the first type of fiber, filtrate diffuses through the confluent monolayer and hollow fibers, and collects into the collecting chamber. The filtrate can then be actively reabsorbed by the renal tubule cells located on the surface of the second type of hollow fibers, which are in contact with the filtrate in the chamber. Filtrate which is not reabsorbed exits collecting chamber through urine outlet port.

The filtration device is suitably implanted either subcutaneously or near the peritoneal cavity. The filtrate formed by this device flows directly into the tubule device which is also suitably implanted either subcutaneously or within the peritoneal cavity. Preferably both devices are implanted peritoneally. This arrangement allows the filtrate to enter the internal compartments of the hollow fiber network which are lined with confluent monolayers of renal tubule cells. The reabsorbate exits into the peritoneal cavity and is reabsorbed into the systemic circulation. After being processed by the tubule device, the final fluid, i.e. urine, is collected by tubing inserted into the ureter to maintain a natural conduit for urine excretion from the individual.

Having generally described this invention, a further understanding can be obtained by reference to certain specific examples which are provided herein below for purposes of illustration only and are not intended to be limiting unless otherwise specified.

EXAMPLES

Example 1

Tubulogenesis from Isolated Single Cells of Adult Mammalian Kidney

Cell Culture

Adult rabbit renal proximal tubule cells were grown in primary culture by techniques previously reported by this laboratory (7,8). The cells were grown in 35 mm Corning culture dishes with serum free hormonally defined Dulbecco's modified Eagle (DME) Ham's F-12 media (1:1, v/v) containing L-glutamine, penicillin/streptomycin, hydrocortisone, insulin, transferrin. Once confluent, cultures were processed for passage. Cultures were treated with 1.0 µM all-trans-retinoic acid (available from Sigma) and 10 nM recombinant human epidermal growth factor (available from Amgen) for 24 hours prior to passage. Cell plates were treated with trypsin for 4 minutes at 37° followed by 0.1% soy bean trypsin inhibitor. The cells were then removed and pelleted by centrifugation at which time various amounts of media were added to make the appropriate dilution of cells. Once passed, the cells were grown in media containing epidermal growth factor (EGF) and retinoic acid (RA) until confluency. In this manner, cells could be harvested at any time after passage for either dispersement and suspension into three-dimensional collagen gels or for continual passage of cells.

Suspension of Cells in Collagen

Collagen Type I (VITROGEN 100, available from Celltrix Labs) was mixed with 10X phosphate buffered saline and pH adjusted to 7.4. Cells ($5\times10^5$) were suspended in 250 ul of media and uniformly dispersed in 750 ul of collagen prior to gelation. An aliquot of the resulting mixture (250 ul) was placed into a chilled Anocell-10 cell culture insert and allowed to set at 37° without $CO_2$ for 45–60 minutes. After gelation, the appropriate culture media was added and the cells were cultured for 7–21 days. Best results occurred with the use of 1.8 mg of collagen/ml.

Recombinant Retrovirus

A high titer, replication defective retrovirus was constructed to encode for the E. coli lac-Z gene (β-galactosidase), thereby providing a convenient assay for the provirus for lineage analysis. A detailed description of the packaging cell line AZ-5. Briefly, the retroviral vector p-mLac Z was transfected into the ecotropic retroviral packaging cell line ψ-cre. Twenty-five clones were isolated and screened for production of p-mlacZ virus by detecting β-galactosidase activity with the chromogenic substrate 5-bromo-4-choro-3-undolyl-βD-galactoside (X-gal) stain; the highest virus-producing celline ψ-crip. Clones producing amphotropic virus were isolated, and the highest titer clone was selected (AZ-5). The AZ-5 virus has a titer of $10^6$ colony forming units (CFUs)/mL, and is free of replication competent virus as determined by a sensitive provirus rescue assay. To harvest virus, the AZ-5 cells were seeded into 10 cm plates ($5\times10^5$ cells per plate) in DMEM containing 10% fetal calf serum and penicillin/streptomycin. Twenty-four hours after seeding the media was changed, and after an additional 24 hours the virus containing supernatant was harvested and filtered through a 0.45 u filter. Renal proximal tubule cells were prepared after growth in primary culture and 2 or 3 serial passages. Under subconfluent conditions, renal tubule cells were exposed to undiluted or diluted stocks of recombinant retrovirus for 24 hours in the presence of Polybrene (8 ug/ml). After transduction the culture medium was then removed and replaced with serum-free, hormonally defined culture medium supplemented with JRA and EGF. Cells were then grown to confluence, removed from culture plates and suspended into collagen gels for 10–14 days.

Histologic Processing

Collagen gel cultures were fixed in situ with 2% glutaraldehyde and Sorenson's buffer (pH 7.2, 310 mOsm). Semithin and thin sections were prepared with standard techniques reported for this laboratory. Thin sections were examined with a Zeiss 9-S2 electron microscope. To process collagen gels for X-gal staining, gels were fixed in 0.5% glutaraldehyde for 2 hours, washed twice with PBS containing 1 mM $MgCl_2$, and incubated with a solution containing 1 mg/ml X-gal in PBS for 24 hours at 37° C. Gels were then rinsed twice with PBS for 10 minutes, followed by addition of 2% glutaraldehyde for 24 hours. Gels were embedded in paraffin, sectioned and processed for light microscopy.

Example 2

Filtration Prototype Based upon Targeted Angiogenesis

The first generation filtration device was constructed using the commercially available AMICON® diafilter minifilter, currently used for continuous arteriovenous hemofiltration in the clinical setting. The device is comprised of polysulfone fibers possessing high ultrafiltration coefficients (sieving coefficients for sodium, vitamin B-12, and inulin greater than 0.95 with a molecular cutoff of approximately 50,000 molecular weight, so that the sieving coefficient for albumin is approximately 0.2). The polysulfone hollow fibers are potted in medical grade silicon rubber and housed in acrylic casing to which the various ports have been attached.

The filtration device was constructed in the following manner. The plastic casing of the cartridge was removed and the hollow fibers were then encased with collagen type I in a mold made from a commercially available gelatin derivative (GELFOAM®) to maintain appropriate cartridge architecture, and various concentrations of angiogenic growth factors (initially FGF-acidic and FGF-basic). After sterilization, the blood input port was capped, thereby providing a single channel to infuse angiogenic substances into and through the hollow fibers, and to collect filtrate transudating from the neovessels, coursing through the extracellular matrix components, and into the semipermeable hollow fibers.

Figure 9A:
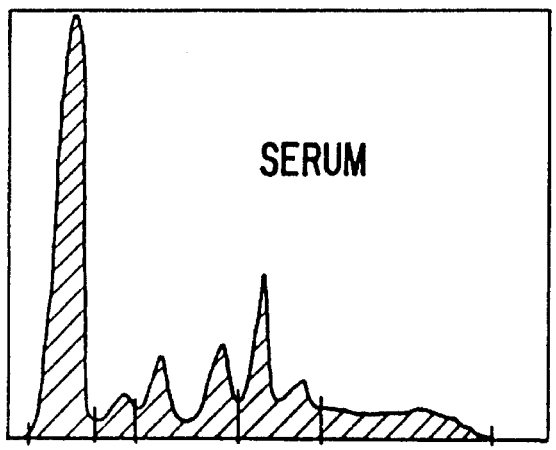
FIG. 9 is protein electrophoresis of rabbit serum (top), filtrate from initial filtration device (middle), and filtrate from second generation filtration device (bottom).
Figure 9B:
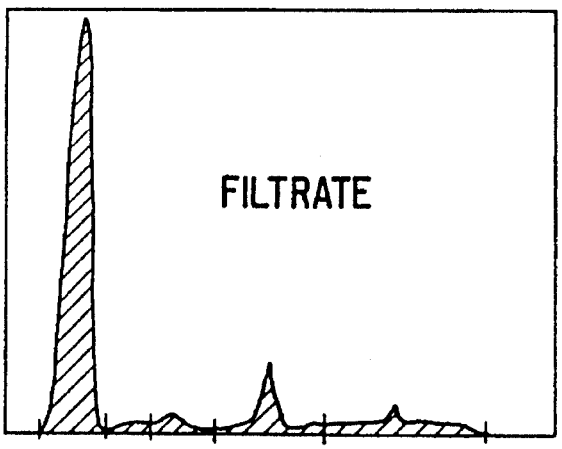

The filtration device was then implanted subcutaneously into an adult rabbit. The single collecting port was connected to tubing which was tunneled subcutaneously to an infusion port placed subcutaneously. Daily injections of FGF-basic (10 ng/ml) in 5 ml aliquots were administered via the infusion port for 14 days at which time collection from the drainage tube was initiated. For collection, the animal was placed in a mild restraining harness, the port was tapped and attached to tubing which drained into a collection vial. Over four hours, hourly time collections of fluid were accomplished and the fluid was then analyzed for BUN, creatinine, electrolytes and albumin content to determine whether its composition was similar to the ultrafiltrate of blood. Spontaneous fluid flow occurred immediately after placement of the collection catheter. Volume flow was 24 ml over the first four hours of collection. Because of the large volume loss occurring during this time interval, the collection was discontinued to prevent volume depletion in this animal. Fluid from the last 60 minutes of fluid flow was then analyzed with the following results. Examination of the electrolyte content of the 4th hour fluid collection demonstrated the following concentrations: $Na^+$=138 mEq/L, $K^+$=4.0 mEq/L, $Cl^-$=107 mEq/L, Total $CO_2$ =17 mEq/L, Creatinine=1.1 g/dl, BUN 20 mg/dl, and glucose 41 mg/dl. These values are identical to plasma levels of normal healthy rabbits. Protein electrophoresis of the fluid demonstrated size selective barrier function, as demonstrated in FIG. 9b.

Comparison electrophoretic profile of proteins in the collected fluid and serum demonstrated the presence of albumin and transferrin, proteins of 50–75,000 MW, but no proteins of larger MW in the collected fluid. This finding was troubling until the observation that sterilization of the polysulfone hollow fibers with ethylene oxide changed the pore size of the fibers to allow albumin leakage during the in vitro testing.

Accordingly, a second generation filtration device was constructed using FRESENIUS F80 polysulfone hollow fibers with high hydraulic permeability characteristics but with a molecular cutoff of 20,000 daltons. In this design, the hollow fibers were assembled as a plate with approximately 100 hollow fibers measuring 10 cm in length, being potted on both ends (FIG. 3b). One end was then cut flush for access to the internal compartments of the hollow fibers. A header of silicon tubing was constructed to fit snugly on the cut surface of the potted hollow fibers; an exit port was connected to the header; and plastic tubing was connected from the exit port to an infusion port.

Figure 9C:
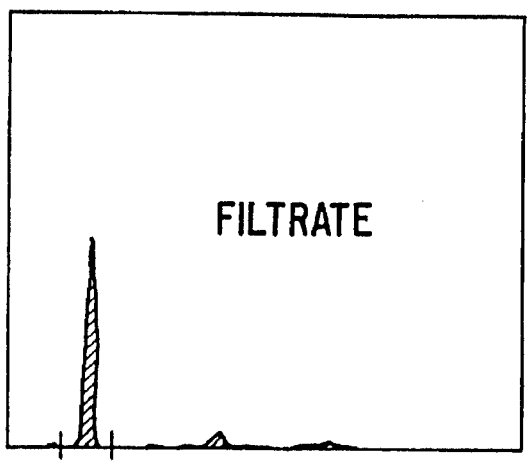

As before, after 2 weeks of FBF-basic administration, the collection port was tapped and spontaneous fluid flow occurred and hourly fluid samples were collected for 5 hours. Total fluid collection over 4 hours was 7 ml with the last 3 collections between 1 and 1.4 ml per hour. The solute content of the final 5th hour collected fluid was $Na^+$=145 mEq/L, $K^+$=4.4 mEq/L, $CL^-$=108 mEq/L, Total $CO_2$ =17 mEq/L, creatinine =1.0 mg/dl, BUN =17 mg/dl-values identical to simultaneous rabbit serum levels. The protein content of the collected fluid was 200 mg/dl which by protein electrophoresis was comprised of only albumin with no other larger protein component (FIG. 9c). Of importance, the simultaneous serum total protein concentration of this rabbit was 4.9 gm/dl with an albumin content of 3.4 gm/dl.

Example 3

Targeted Angiogenesis of Filtration Device

Various iterations of the filtration devices can be envisioned to improve its efficiency: increasing the density of neovessel formation with the persistent and continuous production of angiogenic factors, various extracellular matrix components which possess the ability to both bind angiogenic factors and promote more efficient angiogenic morphogenesis, and implantation of the device in different areas of the animal which may also improve the ultrafiltration property of the neovessels since various capillary networks within the body having differing ultrafiltration coefficients (the kidney greater than the peritoneal cavity, greater than skin, greater than muscle).

Preliminary work with the initial filtration device implant demonstrated that if exogenous administration of FGF-b was discontinued for 2 weeks, spontaneous filtration stopped due to regression of capillary ingrowth around the hollow fiber device. Accordingly, work has proceeded in developing a method to promote continuous targeted angiogenesis in the hollow fiber network with gene transfer. An amphotrophic, replication defective, recombinant retrovirus was constructed utilizing the retroviral vector p-mLacZ which contains a full length coding sequence for fibroblastic growth factor (FGF)-5 and the retroviral packaging cell line ψ-crip. FGF-5 was chosen for several reasons. Unlike FGF-acidic and FGF-basic FGF-5 has a hydrophobic N-terminus in the predicted protein sequence, so that FGF-5 is secretable via the classic secretory pathway. FGF-5 is also mitogenic to mesenchymal cells and has angiogenic potential. Accordingly, using the constructed retroviral vector, p-mFGF5, rabbit renal proximal tubule progenitor cells were transduced with the vector and seeded into three-dimensional collagen gels and allowed to grow in defined media for 7 days. After this time interval, collagen gels were transplanted on chorioallontic membranes (CAM) of 7–9 day old chick embryos for an additional 7 days. The CAM bioassay has been a classic system to assess and quantitate angiogenic responses to various compounds and cells. Transplantation of renal tubule cells transduced with the recombinant retrovirus containing the FGF-5 gene promoted capillary growth into the collagen gel containing the transduced cells. No angiogenesis was observed in collagen gels containing non-transduced cells.

This data allows for the plan to eventually utilize rabbit renal glomerular epithelial cells for transduction with p-mFGF5, allowed by seeding and confluent growth of the transduced cells along the inner surface of the hollow fibers for continuous release of FGF-5 to promote and maintain a capillary network around the hollow fiber bundle. Glomerular, rather than proximal tubule, epithelial cells are chosen, since the direction of fluid transfer of this prototypic device will be vectorially correct. Normal vectorial filtration fluid transfer in the renal glomerulus occurs in vivo from capillary lumen, between glomerular cells, and into the collecting (Bowman's) space of the glomerulus. The utilization of transduced glomerular epithelial cells will mimic this physiologic pathway from capillary lumen, interstitial space, hollow fiber membrane, glomerular epithelial cells and hollow fiber collecting space. The junctional complex between glomerular epithelial cells is leaky enough to allow fluid transfer to occur with high hydraulic convectivity. In contrast, the use of renal proximal tubule cells with their tight junctional complexes would provide a greater barrier to convective fluid flow and, therefore, should not be used in this formulation.

Example 4

Gene Transfer Of Hirudin Into Rabbit Endothelial Cells

A full length cDNA encoding for the hirudin variant HV-2 (Johnson et al., *Seminars in Thrombosis* 15:302–315, 1989)

was constructed utilizing dual asymmetric polymerase chain reaction (PCR) in which four adjacent oligonucleotides of 76 to 89 bases in length having short overlaps of 14 bases were used as primers in a PCR mixture (Sandhu et al., *Biotechniques* 12:14–16, 1992). In constructing this cDNA, a signal sequence for vonWillebrand factor (vWF) was incorporated in frame 5' to the hirudin gene to ensure secretion of hirudin from transduced cells; protein coding sequences were selected based upon optimal codon usage in rabbit and human genetic sequence data (Wada et al., *Nucleic Acids Research* 19:1981–1986, 1992), and appropriate restriction enzyme cut sites 5' and 3' to the cDNA encoding the vWF signal peptide and hirudin HV-2 were introduced for ease of transfer into the retroviral vector. The sequence of the constructed cDNA was confirmed to be the desired sequence by bidirectional cloning utilizing the dideoxy chain termination reaction. Utilizing the retroviral vector pMFG derived from the Moloney murine leukemia tumor virus (Dranoff et al., *Proc. Natl. Acad. Sci U.S.A.* 85:6460–6464, 1988) and the packaging cell line (Danos, O., and R. C. *Proc. Natl. Acad. Sci. U.S.A.* 85:6460–6464, 1988), ψcrip, an amphotropic, replication defective, recombinant retrovirus was constructed containing the required gene sequence. Preliminary work utilizing a recombinant retrovirus, constructed from the vector pMFG containing the lac Z gene which encodes for β-galactosidase and the ψ-crip cell line, at an undiluted titre of $10^6$ CFU/ml demonstrated a transduction efficiency of greater than 30% in rabbit aortic endothelial cells in tissue culture, thereby suggesting that gene transfer of the required cDNA into endothelial cells with this recombinant retrovirus will not be limiting. Experiments are currently underway to assess efficiency of hirudin gene transfer into endothelial cells utilizing this retrovirus and the efficacy of gene transfer with measurement of secreted hirudin activity into the tissue culture supernatant.

Example 5

Filtration Prototype Based Upon Endothelial Cell Layering

Endothelial cell cultures can be adapted from well-established methodology. Twenty-four well cluster plate wells layered with Matrigel can be used. The rabbit can be anesthetized and its abdominal cavity opened. A 2 cm length of abdominal aorta is removed from the rabbit and rinsed three times in PBS containing 50 units/ml of heparin. The vessel can be cleaned carefully with removal of periadventitial fat and connective tissue. The aorta can then be cut into rings of less than 2 mM thickness. The aortic rings can then be placed in the base of the wells on Matrigel and covered with just enough media to keep moist. Suitable media is RPMI-1640, 10% fetal calf serum, and 50 ug/ml of endothelial cell growth supplement (ECGS) with appropriate penicillin/streptomycin additions. Endothelial cells grow as a monolayer on the Matrigel extending from the aortic ring explant. After 4 to 8 days the explant can be removed and the endothelial cells can be allowed to reach confluence. Once confluency is achieved, endothelial cells for passage can be collected by treatment with 2% Dispase in calcium-magnesium free HBSS. To maintain differentiation characteristics, endothelial cells will be utilized for not more than six continuous passages.

The harvested cells will then be seeded into a single hollow fiber contained within a bioreactor. The hollow fiber will either be a polysulfone hollow fiber from AMICON® or a polysulfone hollow fiber from FRESENIUS with a ultrafiltration coefficient greater than 20 mL/hr, Torr and a molecular cutoff of $\leq 60,000$ g/mol. Adaptations to the hollow fiber bioreactor detailed previously will be achieved by adding an adjustable resistance clamp along the perfusion exit tubing to increase hydraulic pressure within the hollow fiber. Connected proximal to this adjustable clamp will be a pressure gauge for measurement of hydraulic pressure within the system. Previous reports of seeding of hollow fibers with permanent epithelial cell lines have demonstrated confluency being achieved within several days after seeding. Once confluency is achieved, hydraulic permeability and albumin exclusion from the filtrate can be measured with radiolabeled inulin and radiolabeled albumin.

Under constant flow rates and with adjustments of the resistance clamp, incremental increases in pressure within the hollow fiber is planned. After each adjustment, timed collections of inulin and albumin movement from intraluminal to bath compartment will be measured to assess the permeability characteristics of the endothelial cell lined hollow fiber. Once the device is functional, planned experiments will test the influence of the various ECM components on the permeability function of the endothelial monolayer. The internal surface of the hollow fiber will be precoated with various types of extracellular matrix components, including collagen type I, collagen type IV, laminin, and Matrigel. Each of these configurations utilizing different matrix components will then be tested for inulin and albumin clearance function using the single hollow fiber bioreactor. In this manner, assessment of the influence of various extracellular matrix components on hydraulic permeability, as assessed by inulin clearance, and albumin exclusion can be measured. Both scanning and transmission electron microscopy will also be accomplished to assess the presence of fenestrations along the endothelial cell lining monolayer.

Additionally, a filtration device in which large number of bundled hollow fibers, each containing confluent monolayers of endothelial cells grown on the appropriate extracellular matrix material, will be produced to establish a large enough device for in vivo testing by attaching the filtration device to an arteriovenous system with high flow characteristics to determine the efficacy of filtration function under systemic pressures. Also, the testing for clotting within these in vivo or ex vivo filtration systems can then be accomplished.

Example 6

Prototype for a Tubule Processing Device

Development of a tubule processing device is dependent upon cell culture methodology for renal proximal tubule progenitor cells and the availability, as detailed above, of a single hollow fiber bioreactor for confluent growth of these cells along the inner surface of the hollow fiber for functional transport testing. The methodology to growth select for renal proximal tubule progenitor cells from adult mammalian tissue is set forth in U.S. Ser. No. 7/844,758, incorporated herein by reference. Adult rabbit renal proximal tubule cells are grown in primary culture (Garlick et al., *J. Invest. Dermatol.* 97(5):824–829, 1991; Humes et al., *Am. J. Physiol.* 262:F540–F545, 1992). Once confluent, the cultures are processed for passage by treatment with 1.0 uM all-trans retinoic acid and 10 nM epidermal growth factor for 24 hours prior to passage. Cell plates are then treated with trypsin for four minutes at 37° C. followed by 0.1% soybean trypsin inhibitor. The cells are then removed and pelleted by centrifugation at which time various amounts of media were added to make the appropriate dilution of cells. Once passed, the cells are grown in media containing epidermal growth factor and retinoic acid until confluency. In this manner, cells can be harvested at any time after passage for either continual passage or utilization for seeding experiments. Prior data has demonstrated that this selective growth conditions after serial passages leads to an enriched population of renal progenitor cells with two important characteristics: An ability to differentiate morphogenically into tubule structures when grown in three-dimensional collagen gels and a high capacity for self renewal with cell lineage analysis with a recombinant retrovirus.

Figure 10:
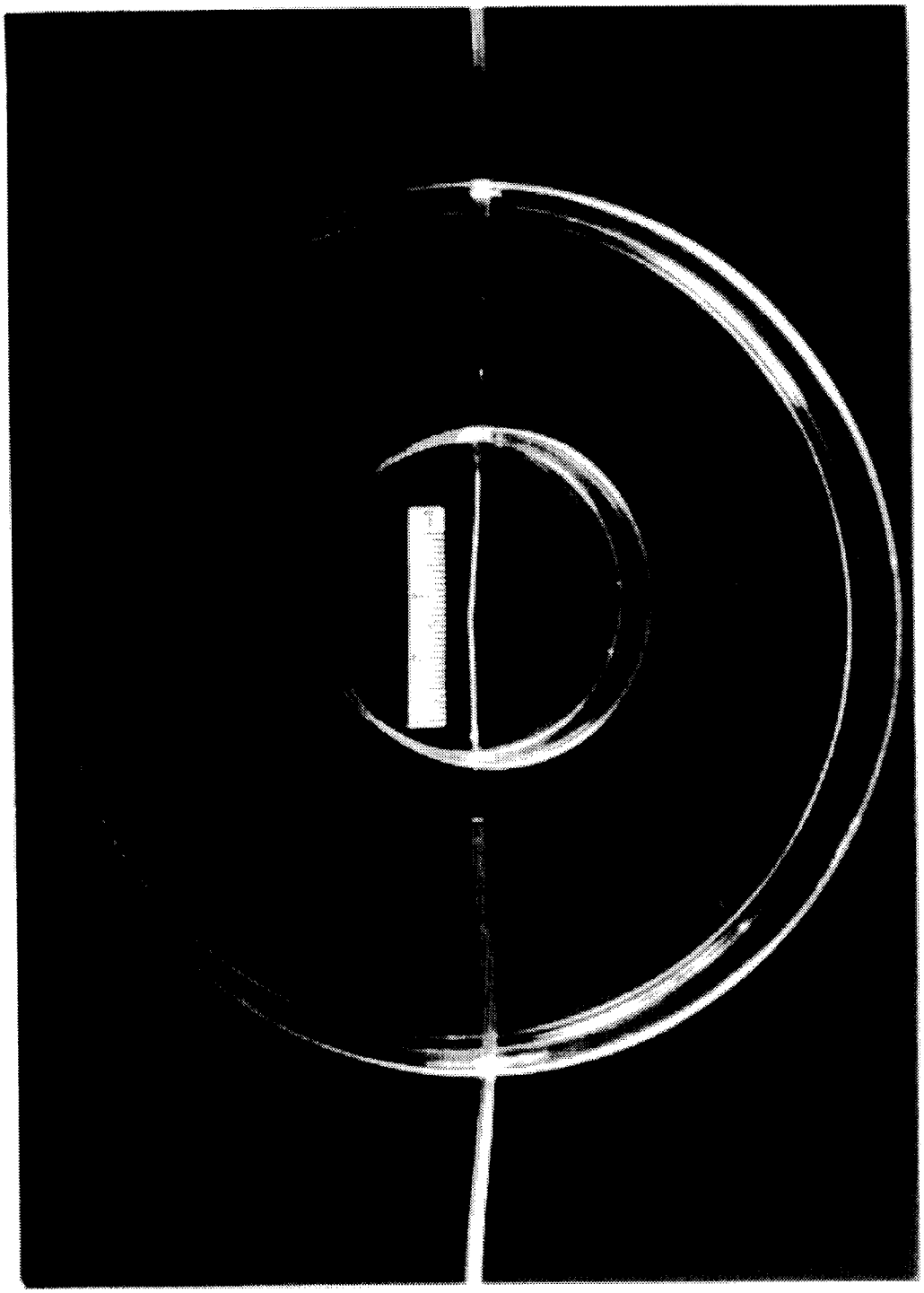
FIG. 10 is a formulation of a single hollow fiber perfusion in vitro test system.

Utilizing these cells in the previously detailed single hollow fiber bioreactor, a single hollow fiber was layered with various matrix components including collagen type I, collagen type IV, laminin, and Matrigel, and then seeded with the renal proximal tubule progenitor cells. After 5–7 days of growth in the bioreactor, confluent growth along the inner surface was achieved with renal progenitor cells. An in vitro test system (see FIG. 10) was established by connecting this fiber to a Harvard pump on the input side and to a collecting vial on the output side. Using this single pass perfusion system, various transport functions characteristic of differentiated proximal tubule function can be assessed using radiolabeled substances. Sodium and water transport can be assessed with inulin. Differentiated transport characteristics of glucose and amino acid reabsorption can be measured with radiolabeled glucose and alanine. Organic acid secretion capabilities of the monolayer can be assessed with para-aminohippurate. To test these transport functions, the single pass perfusion circuit will be employed at a various flow rates less than 1 ml/hour. Radiolabeled inulin at a concentration of 10 µCi/ml will be used as a volume marker for sodium and water reabsorption by the perfused hollow fiber, analogous to the technique used for microperfusion of isolated proximal tubule segments classically described in the nephrology literature (Burg et al., *Am. J. Physiol.* 210(6):1293–1298, 1966; Tune and Burg, *Am. J. Physiol.* 221(2):580–585, 1971; Rabito and Karish, *J. Biol. Chem.* 258(4):2543–2547, 1983; Tune et al., *Am. J. Physiol.* 217(4):1057–1063, 1969; Burg et al., *Am. J. Physiol.* 231(2):627–637, 1976). Amino acid transport will be measured with the use of radiolabeled alanine at a concentration of 1 uCi/ml and a total perfusate concentration of alanine of 0.5 mM. Similarly, glucose transport will be measured using 1 uCi/ml radiolabeled glucose at a total perfusate concentration of 5 mM glucose. Specificity of glucose transport will be assessed with the addition of phlorizin, a specific inhibitor glucose transporter at a concentration of $1 \times 10^{-5}$M. Para-aminohippurate (PAH) secretion rate of the tubule can be assessed by adding $2.4 \times 10^{-5}$M PAH into the bath with a specific activity of approximately 200 uCi/mM. Measurement of radiolabeled PAH in the collected perfusate will demonstrate secretion from bath to lumen along this perfusion circuit. Utilizing this single hollow fiber bioreactor, the influence of ECM components on selective transport characteristics of the monolayer will thus be assessed. Once the optimal growth and matrix conditions for differentiated transport function is identified, the transport characteristics of this epithelial monolayer can be assessed with regards to its correlation to tubule length and diameter of hollow fiber to determine the most efficacious construction required for a bundled hollow fiber device for function in vivo. Additionally, large bundles of hollow fibers will be incorporated into a single device in order to construct a large effective and efficient tubule processing device which will be placed in series to one of the filtration prototypes detailed previously.

Example 7

Functional Vectorial Transport Of A Hollow Fiber Seeded With Renal Tubule Cells

Since a commercially available hollow fiber cartridge for cell growth in bioreactors is available transport function was tested with bundles of hollow fibers rather than single hollow fibers. In this regard, recent experiments have demonstrated functional vectorial transport of a hollow fiber unit seeded with renal tubule cells. An Amicon Vitafiber cartridge was prepared by lining the internal surface of the hollow fibers with laminin. Renal tubule cells were seeded at a density of $10^5$/ml into the intracapillary space with 4 cell infusions separated by 30 minutes and a 90° rotation of the cartridge. The seeded cartridge was connected to the bioreactor perfusion system displayed in FIG. 3 in which the extracapillary space was filled with culture media containing EGF and RA and capped without perfusion and the intracapillary space perfused with similar media at a rate of 4–5 ml/hour. Culture media, both intracapillary and extracapillary, were changed every 2–3 days to maintain adequate metabolic substrates for growth. This perfusion setup was chosen to insure a slightly higher intraluminal hydraulic pressure within the hollow fibers compared to extracapillary space to simulate in vivo conditions and to promote cell attachment along the internal surface of the hollow fibers. After 7 days of growth, the culture media was changed to exclude EGF to promote quiescent conditions. For the acute study, the extracapillary culture medium was changed to contain 4 gm/dl of albumin to provide an increase in oncotic pressure on the basal surface of the renal tubule cells while the luminal perfusion media maintained its relative protein free nature. In the initial experiment just completed, intraluminal perfusion into the hollow fiber system was initiated while the extracapillary space was connected to a collection vial for net volume flux measurements. Net volume flux was found to occur due to the favorable hydraulic and oncotic pressure differences across the lining epithelium from intratubular to extracapillary spaces. At a perfusion rate of 20 ml/hr (approximately 10–15 nl/min/mm), volume collection from the extracapillary space over 30 minute collecting times varied from 15–25% of the perfusion rate, demonstrating that this bioreactor system is able to measure net reabsorptive flux from luminal space to extracapillary space in a quantitative fashion. Because of the high hydraulic conductivity of the polysulfone fibers, it is presently unclear what component of the reabsorbate flux was due to transepithelial hydraulic pressure differences as opposed to osmotic or oncotic pressure differences. To determine the influence of active $Na^+$ transport, which provides the osmotic pressure difference for salt and water flow across the epithelial monolayer, the effect of ouabain (0.1 mM) on net reabsorbate flux in this system is being tested.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A bioartificial filtration device suitable for filtering blood, comprising at least one semipermeable hollow fiber in a chamber defined by a housing, wherein said one surface of said fiber is coated with a layer of endothelial cells, epithelial cells, or a combination thereof, wherein said cells are non-immortalized cells, and wherein said hollow fiber is in fluid communication with blood inlet and outlet, and wherein said housing is elaborated with a blood filtrate outlet.

2. The bioartificial filtration device according to claim 1, wherein said hollow fiber is internally coated with a composition comprising said endothelial, epithelial cells or a combination thereof and at least one extracellular matrix component.

3. The bioartificial filtration device according to claim 1, wherein said hollow fibers are coated internally with a composition comprising said endothelial cells and at least one extracellular matrix component.

4. The bioartificial filtration device according to claim 3, wherein said endothelial cells are transfected with a gene encoding a compound with anticoagulant activity.

5. The bioartificial filtration device according to claim 4, wherein said gene encodes hirudin.

6. The bioartificial filtration device according to claim 4, wherein said gene encodes a peptide with hirudin-like properties.

7. The bioartificial filtration device according to claims 2 or 3, wherein said extracellular matrix component is a member selected from the group consisting of Type I collagen, Type IV collagen, laminin, proteoglycan, fibronectin, and combinations thereof.

8. The bioartificial filtration device according to claim 1, wherein said semipermeable hollow fiber is formed from a biocompatible polymer.

9. The bioartificial filtration device according to claim 8, wherein said biocompatible polymer is selected from the group consisting of polyacrylonitrile, cellulose, polycarbonate, polymethylmethacrylate, polysulphone, cellulose acetate, acrylic copolymer and ethylene vinyl copolymer.

10. The bioartificial filtration device according to claim 1, wherein said semipermeable hollow fiber has a molecular weight cut-off of less than 66,000 Daltons.

11. The bioartificial filtration device according to claim 1, wherein said semipermeable hollow fiber has an ultrafiltration coefficient greater than 20 mL/hr,Torr, m$^2$.

12. The bioartificial filtration device according to claim 11, wherein said semipermeable hollow fiber has an ultrafiltration coefficient of from 20–100 mL/hr,Torr, m$^2$.

13. The bioartificial filtration device according claim 1, comprising a plurality of said coated semipermeable hollow fibers.

14. A bioartificial filtration device suitable for filtering blood, comprising a bundle of semipermeable hollow fibers in a chamber defined by a housing, wherein said fibers are coated internally with a layer of endothelial or epithelial cells, wherein opposite ends of said hollow fibers are connected to perfusion inlet and outlet ports and wherein said housing contains a blood filtrate outlet.

15. A bioartificial filtration device suitable for filtering blood, comprising at least one semipermeable hollow fiber embedded in extracellular matrix, said fiber in fluid communication with a blood filtrate outlet, wherein one end of said hollow fiber is sealed.

16. The bioartificial filtration device according to claim 15, wherein said semipermeable hollow fiber is formed from a biocompatible polymer.

17. The bioartificial filtration device according to claim 16, wherein said biocompatible polymer is selected from the group consisting of polyacrylonitrile, cellulose, polycarbonate, polymethylmethacrylate, polysulphone, cellulose acetate, acrylic copolymer and ethylene vinyl copolymer.

18. The bioartificial filtration device according to claim 15, wherein said semipermeable hollow fiber has a molecular weight cut-off of less than 66,000 Daltons.

19. The bioartificial filtration device according to claim 15, wherein said semipermeable hollow fiber has an ultrafiltration coefficient greater than 20 mL/hr,Torr.

20. The bioartificial filtration device according to claim 19, wherein said semipermeable hollow fiber has an ultrafiltration coefficient of from 20–100 mL/hr,Torr.

21. The bioartificial filtration device according to claim 15, wherein said extracellular matrix is impregnated with an angiogenic factor.

22. The bioartificial filtration device according to claim 15, wherein said filtration device further comprises a means to deliver angiogenic factors into proximity with said fiber.

23. The bioartificial filtration device according to either claim 21 or 22, wherein said angiogenic factors are selected from the group consisting of acidic fibroblast growth factor (FGF), basic FGF, FGF-5 hepatocyte growth factor, and vascular endothelial growth factor.

24. The bioartificial filtration device according to claim 15, comprising a multitude of said coated semipermeable hollow fibers.

25. A bioartificial filtration device suitable for filtering blood, comprising a plurality of semipermeable hollow fibers which are in close proximity to a capillary network, wherein one end of said hollow fibers is sealed, and the opposite end is in fluid communication with a blood filtrate outlet.

26. A bioartificial tubule processing unit suitable for processing blood filtrate, comprising a semipermeable hollow fiber which is coated internally with a layer of renal tubule cells, wherein said fiber is in fluid communication with a blood filtrate inlet and a urine outlet.

27. The bioartificial tubule processing device according to claim 26, wherein said hollow fiber is coated internally with a composition comprising said renal tubule cells and at least one extracellular matrix component.

28. The bioartificial tubule processing device according to claim 27, wherein said extracellular matrix component is a member selected from the group consisting of Type I collagen, Type IV collagen, laminin, Matrigel, proteoglycan, fibronectin, and combinations thereof.

29. The bioartificial tubule processing device according to claim 26, wherein said renal tubule cells are in a confluent monolayer.

30. The bioartificial tubule processing device according to claim 26, wherein said semipermeable hollow fibers are formed from a biocompatible polymer.

31. The bioartificial tubule processing device according to claim 30, wherein said biocompatible polymer is selected from the group consisting of polyacrylonitrile, cellulose, polycarbonate, polymethylmethacrylate, polysulphone, cellulose acetate, acrylic copolymer and ethylene vinyl copolymer.

32. A bioartificial tubule processing device according to claim 27, comprising a plurality of said coated semipermeable hollow fibers.

33. A bioartificial tubule processing device suitable for processing blood filtrate, comprising a plurality of semipermeable hollow fibers which are internally coated with a layer of renal tubule cells, wherein one end of said hollow fibers is connected to a blood filtrate inlet and the opposite end of said hollow fibers is connected to a urine outlet.

34. A bioartificial tubule processing device suitable for processing blood filtrate, comprising a semipermeable hollow fiber in a chamber defined by a housing, wherein said fiber is coated externally with a layer of renal tubule cells, wherein one end of said fiber is sealed and the opposite end of said fiber is in fluid communication with a reabsorbate outlet, and wherein said housing is further elaborated with a blood filtrate inlet and a urine outlet.

35. The bioartificial tubule processing device according to claim 34, wherein said hollow fiber is coated externally with a composition comprising said renal tubule cells and at least one extracellular matrix component.

36. The bioartificial tubule processing device according to claim 35, wherein said extracellular matrix component is a member selected from the group consisting of Type I collagen, Type IV collagen, laminin, Matrigel, proteoglycan, fibronectin, and combinations thereof.

37. The bioartificial tubule processing device according to claim 34, wherein said renal tubule cells are in a confluent monolayer.

38. The bioartificial tubule processing device according to claim 34, wherein said semipermeable hollow fiber is formed from a biocompatible polymer.

39. The bioartificial tubule processing device according to claim 38, wherein said biocompatible polymer is selected from the group consisting of polyacrylonitrile, cellulose, polycarbonate, polymethylmethacrylate, polysulphone, cellulose acetate, acrylic copolymer and ethylene vinyl copolymer.

40. The bioartificial tubule processing device according to 34, comprising a plurality of said hollow fibers.

41. A bioartificial tubule processing device suitable for processing blood filtrate, comprising a plurality of semipermeable hollow fibers in a chamber defined by a housing, wherein said fibers are coated externally with a layer of renal tubule cells, wherein opposite ends of said fibers are connected to a blood filtrate inlet and perfusion outlet, and wherein said housing is further elaborated with a urine outlet.

42. A bioartificial blood purification device comprising a filtration device and a tubule processing device, wherein said filtration device comprises a semipermeable hollow fiber in a chamber defined by a housing, wherein said fiber is coated internally with a layer of endothelial cells, epithelial cells, or a combination thereof, wherein said hollow fiber is in fluid communication with blood inlet and outlet, and wherein said housing is elaborated with a blood filtrate outlet, wherein said filtration device is in fluid communication with a tubule processing device which comprises a semipermeable hollow fiber which is coated internally with a layer of renal tubule cells, wherein said fiber is in fluid communication with a blood filtrate inlet and a urine outlet.

43. The bioartificial blood purification device according to claim 42, wherein said filtration device and said tubule processing device comprise a plurality of said semipermeable hollow fibers.

44. A bioartificial blood purification device comprising a filtration device and a tubule processing device, wherein said filtration device comprises a semipermeable hollow fiber in a chamber defined by a housing, wherein said fiber is coated internally with a layer of endothelial cells, epithelial cells, or a combination thereof, wherein said hollow fiber is in fluid communication with blood inlet and outlet, and wherein said housing is elaborated with a blood filtrate outlet, wherein said filtration device is in fluid communication with said tubule processing device which comprises a semipermeable hollow fiber in a chamber defined by a housing, wherein said fiber is coated externally with a layer of renal tubule cells, wherein one end of said fiber is sealed and the opposite end of said fiber is in fluid communication with a reabsorbate outlet, and wherein said housing is further elaborated with a blood filtrate inlet and a urine outlet.

45. The bioartificial blood purification device according to claim 44, wherein said filtration device and said tubule processing device comprise a plurality of said semipermeable hollow fibers.

46. A bioartificial blood purification device comprising a filtration device and a tubule processing device, wherein said filtration device comprises a semipermeable hollow fiber embedded in extracellular matrix, wherein said fiber is in fluid communication with a blood filtrate outlet and is sealed at one end, and wherein said filtration device is in fluid communication with said tubule processing device which comprises a semipermeable hollow fiber which is coated internally with a layer of renal tubule cells, wherein said fiber is in fluid communication with a blood filtrate inlet and a urine outlet.

47. The bioartificial blood purification device according to claim 46, wherein said filtration device and said tubule processing device comprise a plurality of said semipermeable hollow fibers.

48. A bioartificial blood purification device comprising a filtration device and a tubule processing device, wherein said filtration device comprises a semipermeable hollow fiber embedded in extracellular matrix, wherein said fiber is in fluid communication with a blood filtrate outlet and is sealed at one end, and wherein said filtration device is in fluid communication with said tubule processing device which comprises a semipermeable hollow fiber in a chamber defined by a housing, wherein said fiber is coated externally with a layer of renal tubule cells, wherein one end of said fiber is sealed and the opposite end of said fiber is in fluid communication with a reabsorbate outlet, and wherein said housing is further elaborated with a blood filtrate inlet and a urine outlet.

49. The bioartificial blood purification device according to claim 48, wherein said filtration device and said tubule processing device comprise a plurality of said semipermeable hollow fibers.

50. A bioartificial blood purification device comprising a device comprising a plurality of first and second types of semipermeable hollow fibers in a chamber defined by a housing with a urine outlet, wherein the first type of said fibers provide filtration function, are internally coated with endothelial cells and are in fluid communication with blood inlet and outlet, and wherein said the second type of said fibers provide reabsorption function, are coated externally with a layer of renal tubule cells, and have one end sealed and the opposite end in fluid communication with said perfusion outlet.

51. A bioartificial blood purification device comprising, in fluid communication with each other, (1) a hemodialyzer and (2) a bioartificial tubule processing device comprising a semipermeable hollow fiber which is coated internally with a layer of renal tubule cells, wherein said fiber is in fluid communication with a blood filtrate inlet and a urine outlet.

52. A bioartificial blood purification device comprising, in fluid communication with each other, (1) a hemodialyzer and (2) a bioartificial tubule processing device comprising a semipermeable hollow fiber in a chamber defined by a housing, wherein said fiber is coated externally with a layer of renal tubule cells, wherein one end of said fiber is sealed and the opposite end of said fiber is in fluid communication with a reabsorbate outlet, and wherein said housing is further elaborated with a blood filtrate inlet and a urine outlet.

53. A bioartificial filtration device suitable for filtering blood, comprising:

at least one semipermeable membrane, coated on one surface with a layer of endothelial cells, epithelial cells or a combination thereof, in a chamber defined by a housing containing:
  (i) a perfusion inlet supplying a flow of blood passed, and in fluid communication with, said one surface of said membrane and
  (ii) a perfusion outlet for receiving blood which has flowed over said one surface of said membrane, and
  (iii) a filtrate outlet for receiving filtrate in fluid communication with the surface opposite said cell coated surface of said membrane.

54. A bioartificial tubule processing device suitable for processing blood filtrate, comprising:
  at least one semipermeable membrane, coated on one surface with a layer of renal tubule cells, in a chamber defined by a housing containing:
  (i) a filtrate inlet supplying a flow of blood filtrate passed, and in fluid communication with, said one surface of said membrane and
  (ii) a urine outlet for receiving blood filtrate which has flowed over said one surface of said membrane, and
  (iii) a reabsorbate outlet in fluid communication with the surface opposite said cell coated surface of said membrane.

55. A bioartificial filtration device suitable for filtering blood, comprising a semipermeable hollow fiber in a chamber surrounded by a housing, wherein said fiber is coated with a layer of hirudin, hirudin fragments or hirulog, wherein said fiber is in fluid communication with blood inlet and a blood outlet, and wherein said housing is elaborated with a blood filtrate outlet.

56. The filtration device according to claim 2, wherein hirudin, a hirudin fragment, or hirulog is covalently linked to said fibers.

57. A bioartificial tubule processing unit suitable for processing blood filtrate, comprising a semipermeable hollow fiber which is coated externally with a layer of renal tubule cells, wherein said fiber is in fluid communication with a blood filtrate inlet and a urine outlet.

58. A bioartificial blood purification device comprising a filtration device and a tubule processing device,
  wherein said filtration device comprises at least one semipermeable hollow fiber in a chamber defined by a housing, wherein said one surface of said fiber is coated with a layer of endothelial cells, epithelial cells, or a combination thereof, wherein said cells are non-immortalized cells, and wherein said hollow fiber is in fluid communication with blood inlet and outlet, and wherein said housing is elaborated with a blood filtrate outlet,
  wherein said filtration device is in fluid communication with a tubule processing device which comprises at least one semipermeable hollow fiber which is coated externally with a layer of renal tubule cells, wherein said fiber is in fluid communication with a blood filtrate inlet and a urine outlet.

59. The device of claim 58 wherein said filtration device precedes said tubule processing device in said series.

* * * * *